(12) United States Patent
Schlaepfer

(10) Patent No.: US 7,867,256 B2
(45) Date of Patent: Jan. 11, 2011

(54) DEVICE FOR DYNAMIC STABILIZATION OF BONES OR BONE FRAGMENTS

(75) Inventor: Fridolin Johannes Schlaepfer, Hoelstein (CH)

(73) Assignee: Synthes USA, LLC, West Chester, PA (US)

( * ) Notice: Subject to any disclaimer, the term of this patent is extended or adjusted under 35 U.S.C. 154(b) by 776 days.

(21) Appl. No.: 11/697,911

(22) Filed: Apr. 9, 2007

(65) Prior Publication Data

US 2007/0233095 A1    Oct. 4, 2007

Related U.S. Application Data

(63) Continuation-in-part of application No. PCT/EP2005/003962, filed on Apr. 14, 2005.

(30) Foreign Application Priority Data

Oct. 7, 2004    (DE) .................... 10 2004 048 938

(51) Int. Cl.
*A61B 17/70* (2006.01)
(52) U.S. Cl. ...................... 606/257; 606/259
(58) Field of Classification Search .......... 606/246, 606/250–276, 278, 279
See application file for complete search history.

(56) References Cited

U.S. PATENT DOCUMENTS

| | | |
|---|---|---|
| 4,041,939 A | 8/1977 | Hall |
| 4,369,769 A | 1/1983 | Edwards |
| 4,448,191 A | 5/1984 | Rodnyansky et al. |
| 4,743,260 A | 5/1988 | Burton |
| 4,932,975 A | 6/1990 | Main et al. |
| 5,002,576 A | 3/1991 | Fuhrmann et al. |
| 5,011,497 A | 4/1991 | Persson et al. |
| 5,084,048 A | 1/1992 | Jacob et al. |
| 5,180,393 A | 1/1993 | Commarmond |
| 5,282,863 A | 2/1994 | Burton |
| 5,375,823 A | 12/1994 | Navas |
| 5,413,576 A | 5/1995 | Rivard |
| 5,415,661 A | 5/1995 | Holmes |
| 5,423,816 A | 6/1995 | Lin |
| 5,480,401 A | 1/1996 | Navas |
| 5,488,761 A | 2/1996 | Leone |
| 5,536,268 A | 7/1996 | Griss |
| 5,540,688 A | 7/1996 | Navas |
| 5,562,737 A | 10/1996 | Graf |
| 5,573,520 A | 11/1996 | Schwartz et al. |
| 5,649,925 A | 7/1997 | Alacreu |
| 5,658,286 A | 8/1997 | Sava |
| 5,662,651 A | 9/1997 | Tornier et al. |
| 5,672,175 A | 9/1997 | Martin |

(Continued)

FOREIGN PATENT DOCUMENTS

DE    2821678    11/1979

(Continued)

*Primary Examiner*—Eduardo C Robert
*Assistant Examiner*—Christina Negrelli
(74) *Attorney, Agent, or Firm*—Stroock & Stroock & Lavan, LLP

(57) ABSTRACT

A device for dynamic stabilization of bones or bone fragments comprising at least one anchor member for attachment to vertebrae having an opening configured to receive a longitudinal member; and the longitudinal member being viscoelastically deformable and having a predetermined bending resilience.

11 Claims, 19 Drawing Sheets

U.S. PATENT DOCUMENTS

| | | | |
|---|---|---|---|
| 5,681,311 A | 10/1997 | Foley et al. | |
| 5,713,900 A | 2/1998 | Benzel et al. | |
| 5,725,582 A | 3/1998 | Bevan et al. | |
| 5,733,284 A | 3/1998 | Martin | |
| 5,814,046 A | 9/1998 | Hopf | |
| RE36,221 E | 6/1999 | Breard et al. | |
| 6,053,922 A | 4/2000 | Krause et al. | |
| 6,241,730 B1 | 6/2001 | Alby | |
| 6,267,764 B1 | 7/2001 | Elberg | |
| 6,290,700 B1 | 9/2001 | Schmotzer | |
| 6,293,949 B1 | 9/2001 | Justis et al. | |
| 6,296,644 B1 | 10/2001 | Saurat et al. | |
| 6,337,142 B2 | 1/2002 | Harder et al. | |
| 6,402,750 B1 | 6/2002 | Atkinson et al. | |
| 6,440,169 B1 | 8/2002 | Elberg et al. | |
| 6,447,518 B1 | 9/2002 | Krause et al. | |
| 6,488,682 B2 | 12/2002 | Kikuchi et al. | |
| 6,554,831 B1 | 4/2003 | Rivard et al. | |
| 6,585,769 B1 | 7/2003 | Muhanna et al. | |
| 6,626,905 B1 | 9/2003 | Schmiel et al. | |
| 6,626,909 B2 | 9/2003 | Chin | |
| 6,645,207 B2 | 11/2003 | Dixon et al. | |
| 6,652,585 B2 | 11/2003 | Lange | |
| 6,682,533 B1 | 1/2004 | Dinsdale et al. | |
| 6,706,044 B2 | 3/2004 | Kuslich et al. | |
| 6,749,614 B2 | 6/2004 | Teitelbaum et al. | |
| 6,783,527 B2 | 8/2004 | Drewry et al. | |
| 6,835,205 B2 | 12/2004 | Atkinson et al. | |
| 6,884,241 B2 | 4/2005 | Bertranou et al. | |
| 6,966,910 B2 | 11/2005 | Ritland | |
| 6,986,771 B2 | 1/2006 | Paul et al. | |
| 6,989,011 B2 * | 1/2006 | Paul et al. | 606/250 |
| 7,083,621 B2 | 8/2006 | Shaolian et al. | |
| 7,094,237 B2 | 8/2006 | Gradel et al. | |
| 7,097,648 B1 | 8/2006 | Globerman et al. | |
| 7,125,410 B2 | 10/2006 | Freudiger | |
| 7,229,441 B2 | 6/2007 | Trieu et al. | |
| 7,326,210 B2 * | 2/2008 | Jahng et al. | 606/86 A |
| 7,335,200 B2 | 2/2008 | Carli | |
| 7,556,639 B2 | 7/2009 | Rothman et al. | |
| 2002/0035366 A1 | 3/2002 | Walder et al. | |
| 2002/0055740 A1 | 5/2002 | Lieberman | |
| 2002/0087159 A1 | 7/2002 | Thomas | |
| 2002/0123750 A1 | 9/2002 | Eisermann et al. | |
| 2003/0032958 A1 | 2/2003 | Soubeiran | |
| 2003/0040746 A1 | 2/2003 | Mitchell et al. | |
| 2003/0088251 A1 | 5/2003 | Braun et al. | |
| 2003/0109880 A1 | 6/2003 | Shirado et al. | |
| 2003/0171749 A1 | 9/2003 | Le Couedic et al. | |
| 2003/0195514 A1 | 10/2003 | Trieu et al. | |
| 2003/0220643 A1 | 11/2003 | Ferree | |
| 2004/0049189 A1 | 3/2004 | LeCouedic et al. | |
| 2004/0049190 A1 | 3/2004 | Biedermann et al. | |
| 2004/0143264 A1 | 7/2004 | McAfee | |
| 2004/0147928 A1 | 7/2004 | Landry et al. | |
| 2004/0215191 A1 | 10/2004 | Kitchen | |
| 2004/0215193 A1 | 10/2004 | Shaolian et al. | |
| 2004/0236329 A1 | 11/2004 | Panjabi | |
| 2004/0267260 A1 | 12/2004 | Mack et al. | |
| 2005/0033295 A1 | 2/2005 | Wisnewski | |
| 2005/0049708 A1 | 3/2005 | Atkinson et al. | |
| 2005/0065516 A1 | 3/2005 | Jahng | |
| 2005/0085815 A1 | 4/2005 | Harms et al. | |
| 2005/0090822 A1 | 4/2005 | DiPoto | |
| 2005/0101957 A1 | 5/2005 | Buskirk et al. | |
| 2005/0113927 A1 | 5/2005 | Malek | |
| 2005/0131407 A1 | 6/2005 | Sicvol et al. | |
| 2005/0154390 A1 | 7/2005 | Biedermann et al. | |
| 2005/0165396 A1 | 7/2005 | Fortin et al. | |
| 2005/0171539 A1 | 8/2005 | Braun et al. | |
| 2005/0171540 A1 | 8/2005 | Lim et al. | |
| 2005/0171543 A1 | 8/2005 | Timm et al. | |
| 2005/0177156 A1 | 8/2005 | Timm et al. | |
| 2005/0177157 A1 | 8/2005 | Jahng | |
| 2005/0182401 A1 | 8/2005 | Timm et al. | |
| 2005/0182409 A1 | 8/2005 | Callahan et al. | |
| 2005/0203511 A1 | 9/2005 | Wilson-MacDonald et al. | |
| 2005/0203513 A1 | 9/2005 | Jahng et al. | |
| 2005/0203517 A1 | 9/2005 | Jahng et al. | |
| 2005/0203519 A1 | 9/2005 | Harms et al. | |
| 2005/0222569 A1 | 10/2005 | Panjabi | |
| 2005/0228381 A1 | 10/2005 | Kirschman | |
| 2005/0245930 A1 | 11/2005 | Timm et al. | |
| 2005/0261682 A1 | 11/2005 | Ferree | |
| 2005/0261685 A1 | 11/2005 | Fortin et al. | |
| 2005/0261686 A1 | 11/2005 | Paul | |
| 2005/0277922 A1 | 12/2005 | Trieu et al. | |
| 2005/0288670 A1 | 12/2005 | Panjabi et al. | |
| 2005/0288672 A1 | 12/2005 | Ferree | |
| 2006/0015100 A1 | 1/2006 | Panjabi et al. | |
| 2006/0036240 A1 | 2/2006 | Colleran et al. | |
| 2006/0084982 A1 | 4/2006 | Kim | |
| 2006/0111715 A1 | 5/2006 | Jackson | |
| 2006/0129147 A1 | 6/2006 | Biedermann et al. | |
| 2006/0142758 A1 | 6/2006 | Petit | |
| 2006/0142760 A1 | 6/2006 | McDonnell | |
| 2006/0149238 A1 | 7/2006 | Sherman et al. | |
| 2006/0189983 A1 | 8/2006 | Fallin et al. | |
| 2006/0189984 A1 | 8/2006 | Fallin et al. | |
| 2006/0212033 A1 | 9/2006 | Rothman et al. | |
| 2006/0229612 A1 | 10/2006 | Rothman et al. | |
| 2006/0240533 A1 | 10/2006 | Sengupta et al. | |
| 2006/0260483 A1 | 11/2006 | Hartmann et al. | |
| 2006/0264940 A1 | 11/2006 | Hartmann | |
| 2006/0293657 A1 | 12/2006 | Hartmann | |
| 2007/0016193 A1 | 1/2007 | Ritland | |
| 2007/0073293 A1 | 3/2007 | Martz et al. | |
| 2007/0123865 A1 | 5/2007 | Schlapfer et al. | |
| 2007/0129729 A1 | 6/2007 | Petit et al. | |
| 2007/0149909 A1 | 6/2007 | Fortin et al. | |
| 2007/0198088 A1 | 8/2007 | Biedermann et al. | |
| 2008/0195149 A1 | 8/2008 | Burke | |

FOREIGN PATENT DOCUMENTS

| | | |
|---|---|---|
| DE | 4109941 | 10/1992 |
| DE | 4239716 | 8/1994 |
| EP | 0677277 | 3/1995 |
| EP | 0669109 | 8/1995 |
| FR | 2702363 | 3/1993 |
| FR | 2717370 | 9/1995 |
| FR | 2718946 | 10/1995 |
| FR | 2799949 | 4/2001 |
| GB | 2382304 | 5/2003 |
| JP | 09108247 | 4/1997 |
| JP | 2002224131 | 8/2002 |
| WO | WO 2005/044117 | 5/2005 |
| WO | WO 2005/039454 | 6/2005 |
| WO | WO 2005/092222 | 10/2005 |
| WO | WO 2005/094704 | 10/2005 |
| WO | WO 2005/110257 | 11/2005 |

* cited by examiner

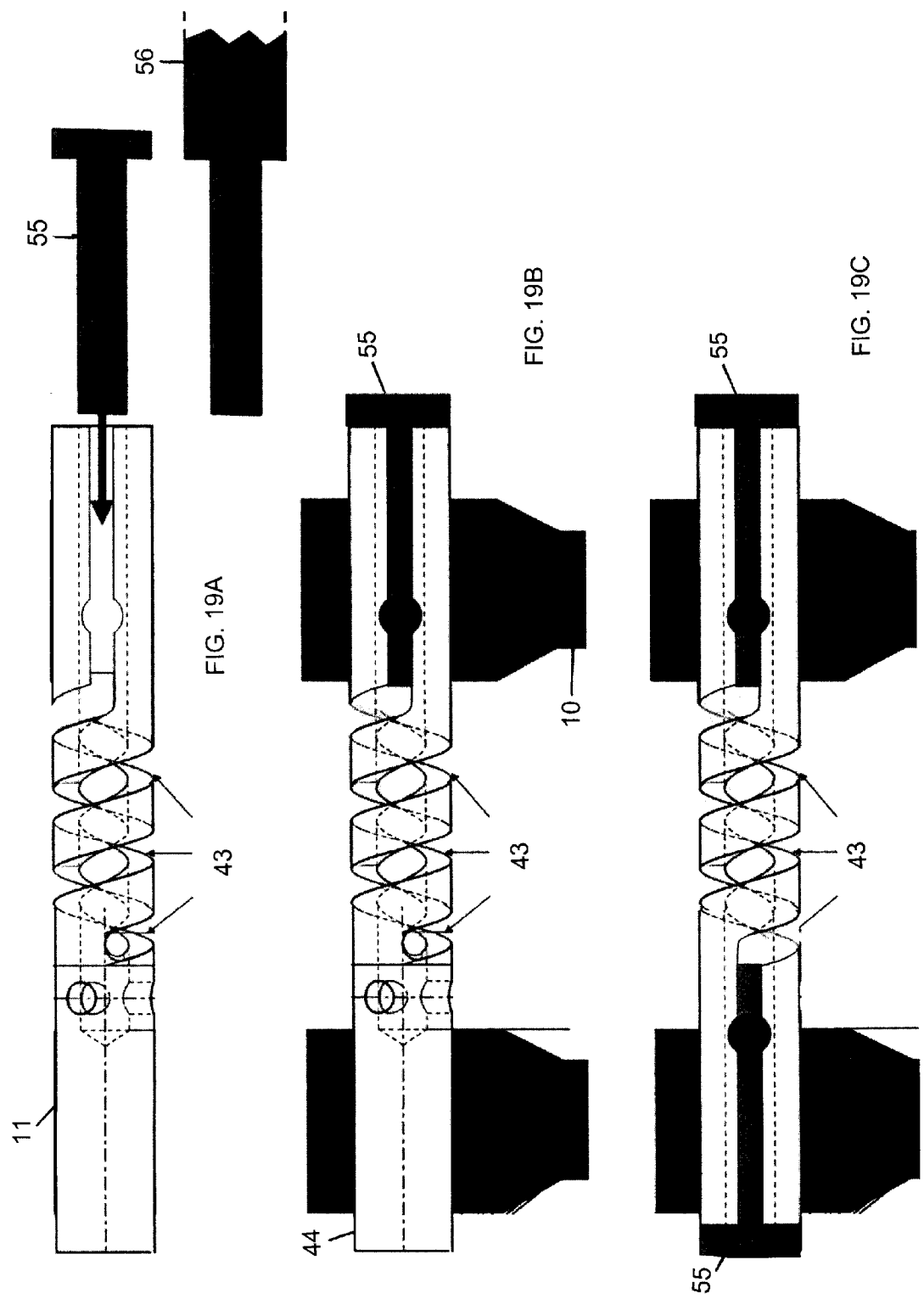

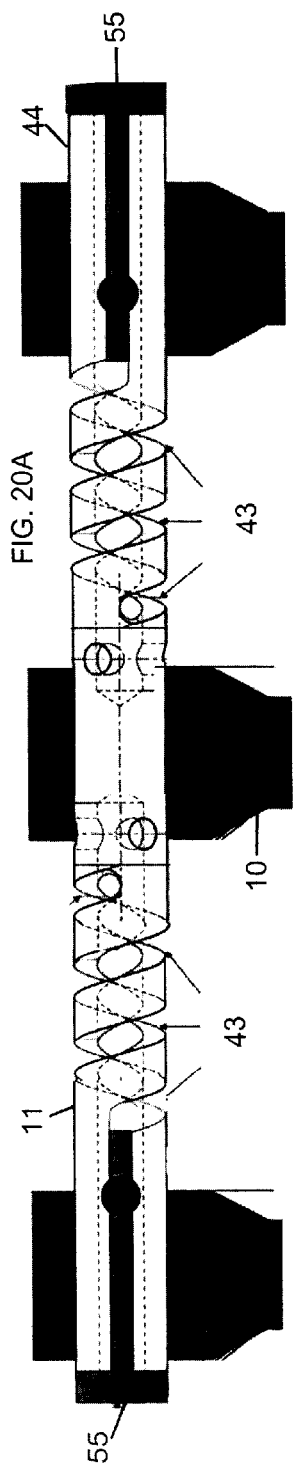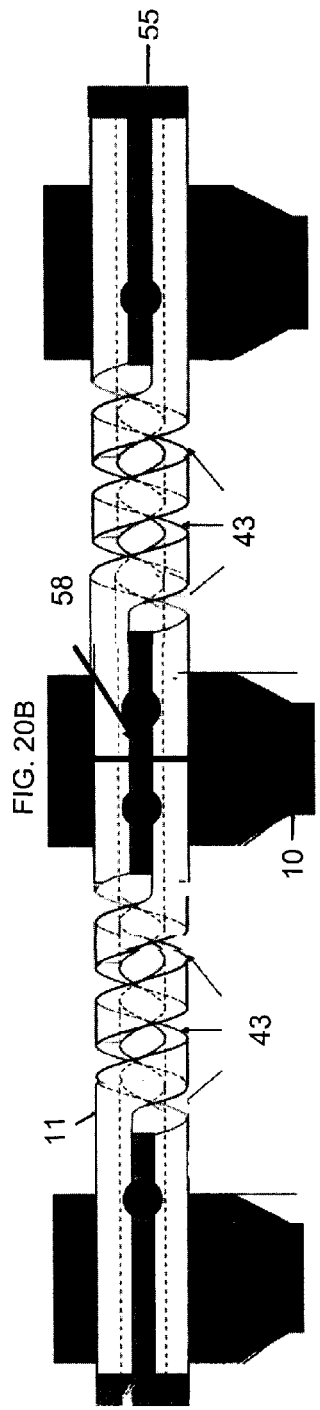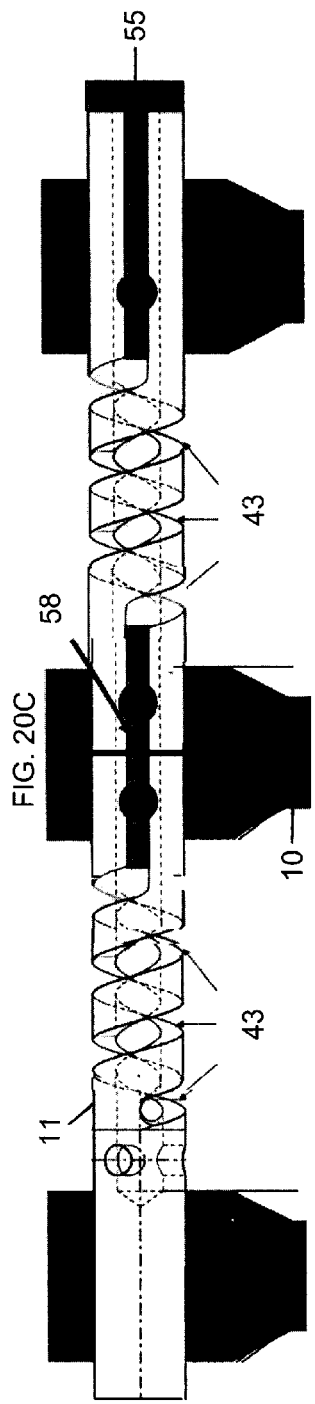

DEVICE FOR DYNAMIC STABILIZATION OF BONES OR BONE FRAGMENTS

CROSS-REFERENCE TO RELATED APPLICATIONS

This is a continuation-in-part of pending International Application No. PCT/EP2005/003962, filed Apr. 14, 2005, which claims the benefit of German Patent Application No. 10 2004 048 938.6, filed Oct. 7, 2004, the entire contents of both of which are expressly incorporated herein by reference thereto.

FIELD OF THE INVENTION

The present invention relates to a device for dynamic stabilization of bones or bone fragments, especially vertebrae of the back, having at least one longitudinal member fixable to the vertebrae.

BACKGROUND OF THE INVENTION

Principal indications for dynamic, especially posteriorly performed, fixation are age- and/or disease-related decay (degeneration) of the integrity of the spine structures, inflammation and/or injuries in the region of the intervertebral disc, of the ligamentous apparatus, of the facet joints and/or of the subchondral bone.

Posterior dynamic fixation systems have the function of modifying the pattern of movement in the segment of spine in question that the pain caused by chemical irritation (material of the nucleus in contact with nerve structures) and/or by mechanical irritation (hypermobility) disappears and the metabolism of the structures is preserved or restored.

Clinical experience with existing posterior dynamic fixation systems as described, for example, in EP 0 669 109 B1 and in the manual "Fixateur externe" (authors: B. G. Weber and F. Mageri, Springer-Verlag 1985, page 290-336) shows that it is advantageous for a posterior dynamic fixation system to be flexible in respect of bending and rigid in respect of compression (buckling), shear and rotation. A system must accordingly be dimensioned for maximum deformation with regard to flexion and for maximum loading with regard to buckling, shear and rotation. In order to be able to combine these intrinsically contradictory conditions, it has already been proposed to manufacture the longitudinal members from a biocompatible high-performance plastics material. Because of the very low modulus of elasticity of the high-performance plastics materials compared to titanium and steel, the longitudinal members have to be of relatively thick construction compared to the longitudinal members conventionally manufactured from clinically used metal, which although having a positive effect on the resistance to shear and to buckling is detrimental to flexibility.

In addition, when using conventional biocompatible high-performance plastics material for longitudinal members, it is problematic that the plastics material in the mechanical fixing "creeps away" at the clamping sites after a relatively short time under the forces occurring therein, with the consequence that re-fixing or even re-implantation becomes necessary.

The possibility of being able to bend longitudinal members is of great importance especially in the case of posterior stabilization by means of pedicle screws, because the anatomical conditions are often such that the pedicle screws screwed through the pedicles and into the vertebrae are misaligned. In order that the longitudinal members can nevertheless be connected to the pedicle screws in as stress-free manner as possible, it must be possible for the shape of the longitudinal members to be matched in situ to the position and orientation of the pedicle screws. In the case of polyaxial pedicle screws, the bending adjustment can be limited to one plane, whereas in the case of monoaxial pedicle screws the longitudinal members have to undergo bending adjustment in three dimensions.

A further constructional form for a dynamic fixation system is proposed in EP 0 690 701 B 1. This last-mentioned system comprises a connecting rod, the extremities of which are fixable to two neighboring vertebrae and which has a curved central portion so that it is resiliency yielding within certain limits. Otherwise, the connecting rod is not modifiable in respect of how it is shaped.

Also, WO 01/45576 A1 proposes a dynamic stabilization system comprising a longitudinal member having two metallic end portions which are fixable in complementary accommodation apertures within the heads of two neighboring pedicle screws. Arranged between the two end portions is an articulation member which is resiliency yielding in the longitudinal direction, preferably made of resiliency yielding material. The two end portions of the longitudinal member are rigid. In addition to that articulation member, the arrangement of a resilient band between two pedicle screws is proposed, which extends parallel to the resilient articulation member. Otherwise, in the case of that arrangement too, the articulation member is, in respect of its longitudinal extension, predetermined during manufacture, that is to say it cannot be modified.

Mention should also be made finally of the arrangement according to FR 2 799 949, which is characterized in that the longitudinal member is in the form of a spring element, for example in the form of a leaf spring having a meandering curve shape.

Also, the longitudinal member in the case of the arrangement according to WO 98/22033 A1 comprises a spring element which retains its predetermined shape.

Also, EP 1 364 622 A1 describes a resilient stabilization system for spines which consists of a resiliently flexible connecting element or longitudinal member which can be passed through the apertures of a plurality of pedicle screws having offset aperture axes and anchored. That connecting element or longitudinal member should preferably be made of a resiliently flexible biocompatible material, preferably plastics material. Aromatic polycarbonate-polyurethane is mentioned as being especially advantageous. This is obtainable as a commercial product, for example under the Trade Mark BIONATE® from Polymer Technology Group, 2810 7th Street, Berkley, Calif. 94710 USA and CHRONOFLEX® C from CardioTech International Inc., 78E Olympia Ave., Woburn, Mass. 01801-2057, USA. The known connecting element or longitudinal member should have sufficient bending resilience about all axes of its cross-section to allow its insertion even into apertures of screw heads that do not lie on one axis but on a line of any desired course or that are naturally offset in various directions because of differing vertebral arrangements.

The integration of spring elements into a longitudinal member is also described in GB 2 382 304 A, U.S. Pat. No. 5,480,401, DE 42 39 716 C1, FR 2 827 498 A1, EP 0919 199 A2 or JP 2002/224131. It is common to all these last-mentioned arrangements, however, that they have a relatively complicated mode of construction, that being the case, more specifically, because the mentioned spring elements are integrated as additional components or structural units. In that prior art, the spring elements are not intrinsic to the longitudinal member.

The present invention is based on the problem of providing a device for dynamic stabilization of bones or bone fragments, especially vertebrae of the back, having at least one longitudinal member fixable to the vertebrae, which longitudinal member can be matched without complication to the very great variety of stations for implantation without the dynamic being lost and can be firmly fixed lastingly, especially to so-called pedicle screws.

SUMMARY OF THE INVENTION

The problem is solved in accordance with the invention by the characterizing features of a device for dynamic stabilization of bones or bone fragments comprising: at least one anchor member for attachment to vertebrae having an opening configured to received a longitudinal member; and the longitudinal member being viscoelastically deformable and having a predetermined bending resilience comprising a biocompatible plastics material, whereby the plastics material provides for viscous deformability, and a biocompatible metal, whereby the metal provides for resiliently flexible deformability.

The longitudinal member preferably is "viscoelastically" deformable and in each shape state has a predetermined bending resilience. The latter should be imparted especially by a metal portion whereas otherwise the longitudinal member is made principally of plastics material that is tolerable to humans, especially of polycarbonate-urethane or PCU, as is commercially available, for example, under the Trade Mark BIONATE®. The longitudinal member is therefore specifically in the form of a compound construction and consists, on the one hand, of plastics material and, on the other hand, of metal that is tolerable to humans, especially titanium or titanium alloy, the plastics material being primarily responsible for the viscous deformability and the metal being primarily responsible for the bending resilience.

As already mentioned, conventional biocompatible plastics materials have the disadvantage that, after being subjected to mechanical pressure for a relatively long period, they yield to that pressure and actually "creep away" under that element of pressure. There is accordingly a risk of the implant becoming loose with obviously disadvantageous consequences. In order to resolve that problem without otherwise losing the afore-mentioned disadvantages, metal is provided, in accordance with the invention, at the clamping sites of the longitudinal member. Clamping is accordingly carried out directly at the metal of the longitudinal member so that the afore-mentioned problem no longer occurs.

Preferred, advantageous material properties of the plastics material that is tolerable to humans or biocompatible are:

| | |
|---|---|
| tensile strength at 50% elongation | about 650-5500 psi |
| tensile strength at 100% elongation | about 900-6000 psi |
| ultimate tensile strength | about 6500-11000 psi |
| ultimate limit of elongation | about 250%-600% |
| modulus of elasticity | about 4000-270000 psi |
| bending stress on 5% deflection | about 150-11000 psi. |

It is also advantageous for the plastics material to have a temperature expansion coefficient ($\times 10^6$) of 90/° C. to 150/° C.

Alternatively, besides polycarbonate-urethane (PCU), the plastics portion can also consist of polyurethane, silicone-urethane copolymer or like material or a mixture thereof. The preferred criteria is that the parameters mentioned above are present or that the material has similar properties to PCU.

The dimensions and the proportions of plastics material and metal are preferably so selected that the longitudinal member, when held at one extremity, can be resiliently deflected, within a predetermined shape state, about an angle of 5° to 12°, especially about 7° to 9°, over a length which corresponds to the spacing between two neighboring vertebrae or about 2-5 cm. To be resiliently deflected means that, after deflection, the longitudinal member or the corresponding portion of the longitudinal member restores itself 100% automatically after deflection.

It should be mentioned at this point that the device preferably is also suitable for anterior implantation when it is necessary for the point of rotation of the spine segment in question to be moved anteriorly.

As a result of the compound construction it is also possible to reduce the dimensions of the longitudinal member consisting primarily of high-performance plastics material to a minimum, that is to say for it to be made substantially smaller than a longitudinal member were it to be made exclusively from biocompatible high-performance plastics material.

In addition, the metal portion on the one hand should be so dimensioned that its critical bending angle is greater than or equal to the maximum bending angle of the stabilized vertebra that is present in association with the dynamic fixation system and on the other hand should be so constructed that the longitudinal member remains dimensionally stable after the in situ bending adjustment.

DE 93 08 770 U1 describes a plastics rod having a metal core. That plastics rod serves as a test rod or template in order to be able to match the shape of the longitudinal members to the position and orientation of the pedicle screws in optimum manner. For that purpose it must be possible for the shape of the test rod to be adjusted by hand in situ in the patient. The test rod accordingly consists of a soft plastics material (for example, silicone) and a metal rod that can readily be plastically deformed (for example, pure aluminum). When the test rod has the same external diameter as the longitudinal member, the test rod exactly reproduces the shape required for it to be possible to insert the longitudinal member in the pedicle screws in a stress-free manner. The present invention differs from the teaching according to DE 93 08 770 U1 on account of the above-defined condition that:

a) the at least one longitudinal member is plastically deformable, by application of a pre-specified bending force, from a first shape state "A" to a second, alternative shape state "B", the bending force required being substantially greater than the peak forces occurring in vivo, and b) the at least one longitudinal member is, within the particular stable shape states, resiliently flexible, that being the case, more specifically, within the limits set by the mechanical interplay between the fixation system and the segment of spine, which limits define a so-called "resilient flexing range".

The longitudinal member is accordingly so dimensioned that the biocompatible high-performance plastics material can be lastingly plastically deformed using appropriate forces whilst, in the deformed state, it should have sufficient bending resilience. That bending resilience is imparted to the plastics material by the metal, which additionally has the advantage and purpose of defining "creep-proof" pressure sites or clamping sites for the longitudinal member.

It should also be mentioned at this point that the longitudinal member should be so constructed that it is as rigid as possible with regard to compression and shear forces occurring in vivo and so constructed that the construct consisting of longitudinal member and anchoring means is substantially resistant to torsion. In that condition the longitudinal member contributes to the alleviation of pain and to the healing process.

The longitudinal member can be in the form of a flat band or strip or, preferably, can have a rotationally symmetrical, circular, polygon-like or elliptical cross-section, the cross-section remaining constant over the entire length in the longitudinal direction of the longitudinal member, varying in accordance with a mathematically describable rule and/or changing in abrupt manner. To that extent, as many degrees of freedom as possible should be provided.

In addition, it should be ensured that the longitudinal member is so dimensioned that, in the mentioned "resilient flexing range", the surface stress is preferably below the dynamic breaking stress. This also applies to the individual components of the longitudinal member.

In addition, the aim is to make available a dynamic stabilization system that is based on following fundamental considerations:

The purpose in the present case is to develop a dynamic pedicle screw system, suitable for posterior insertion, which does not fuse pathologically changed spine segments but rather supports the particular structures in their function in a controlled manner.

As already mentioned above, principal indications for a dynamic system are diseases, inflammation and/or injuries in the region of the intervertebral disc, of the ligamentous apparatus, of the facet joints and/or of the subchondral bone. In those situations it is important to modify the loading pattern in the particular area so that the pathological condition at least does not deteriorate. Healing would be ideal but, at least in the case of degenerative diseases, that may not be possible.

The aim of the dynamic system is, however, not only to freeze the pathological condition or possibly to bring about healing but to form, together with the spinal structures concerned, a unit, consisting of the dynamic system and the spinal structures, which promotes the proper taking in of nutrients by the bone structures and the surrounding tissues.

As soon as a pedicle screw system is inserted from a posterior direction, the point of rotation of the movement segment concerned may be automatically displaced from, and potentially outside of the intervertebral disc in a posterior direction, should it still be flexible. Posterior displacement of the point of rotation into the region of the posterior facet joints can have the following effects, depending on the pathology:

1. Source of Pain: "Posterior Facet Joints":

Depending on the position of the posteriorly displaced center of rotation relative to the posterior facet joints and on the axial compressibility of the system, movement in the joints is more or less dramatically reduced. By that means, the preconditions are created for a degeneratively changed joint to be able to recover as a result of missing hyaline joint cartilage being replaced at least in theory by fibrous cartilage (Salter's passive motion principle). A precondition of recovery is, however, that the system can be implanted in a stress-free manner.

2. Source of Pain: "Posterior Annulus" of the Intervertebral Disc; Lordosis and Intervertebral Disc Height Preserved:

Tears can occur in the posterior annulus of the intervertebral disc as a result of traumatic developments or degenerative changes. These tears often start from the nucleus and penetrate ever farther towards the outer, innervated edge of the annulus. Magnetic resonance imaging (MRI) allows identification of pockets of liquid in the region of the aforementioned tears. These so-called "hot spots" can be an indication of an inflammatory process in the region of the posterior annulus. Inflammation can occur, inter alia, in that region where granulation tissue growing in from the outside and/or nerve endings also meet nuclear material pushing through from the inside through tears in the annulus (physiological pain). The continuous subsequent flow of nuclear material permanently contributes to that inflammation process.

Theoretically, however, inflammation is not absolutely necessary in order to produce pain; rather, the mechanical pressure of a pocket of liquid on afferent nerve endings can alone cause pain. Suitable stabilization can halt the inflammation process and even trigger healing.

This Gives Rise to the Following Considerations:

As a result of the posterior displacement of the point of rotation of the spine segment, its range of movement in flexion and extension is dramatically reduced and the axial force acting on the intervertebral disc is uniformly distributed over the whole of the intervertebral disc. As a result, with "global" flexion/extension of the patient, the nuclear material is no longer squeezed to and fro, that is to say less nuclear material, which stimulates the inflammation process, is pressed through tears in the posterior annulus and against the inflammation site. As a result, the preconditions are created for healing of the inflammation and for the start of a repair process.

3. Problem: "Primary Disc Hernia":

In a disc hernia a connection exists between the nucleus and the surroundings of the annulus. As a result, nuclear material can subsequently flow continuously through tears in the annulus. In a nucleotomy, the discharged material and also material from the nucleus are removed, the latter to avoid a secondary disc hernia. As a result, the lesion of the posterior annulus is made larger operatively.

In this case too, posterior displacement of the point of rotation of the spine segment reduces subsequent flow of nuclear material. The disc hernia can no longer grow, and discharged material, if it has not already been removed operatively, is encapsulated and is reabsorbed by the body. A repair process may take place at the posterior annulus.

Accordingly, in the case of a primary disc hernia a dynamic system has the advantage, at least theoretically, that operative intervention can be minimized (it is not necessary to open the epidural space and cause additional damage to the annulus). As a result, optimum conditions can be created for healing and restoration of the function of the intervertebral disc.

4. Source of Pain: "Posterior Annulus of the Intervertebral Disc" (Collapse of Intervertebral Disc):

Pain in the posterior annulus can be caused by delamination of the annulus. Delamination of the posterior annulus occurs when the nucleus is dehydrated and the intervertebral disc has accordingly collapsed. As a result of the posterior displacement of the point of rotation to the region behind the posterior facet joints, the pressure in the region of the posterior annulus is reduced, which prevents further delamination of the posterior annulus. As a result the preconditions are created for healing/scarring of the annulus, provided of course that the annulus has an appropriate healing potential.

5. Source of Pain: "Upper Plate/Subchondral Bone":

Using MRI it is possible to detect changes in the liquid metabolism in the subchondral bone of the vertebra. In particular, it is also possible to ascertain a sclerotic change in the bony upper plate, which indicates restriction or stoppage of the nutritional supply to the intervertebral disc. A sclerotic change in the upper plate is not readily reversible. The degenerative "downfall" of the intervertebral disc is pre-programmed.

Another possibility is an increased liquid content, for which there are two explanations:

a) inflammation in the subchondral region leading to inflammatory pain;
b) backing-up as a result of "blockage" of the connecting channels in the cartilaginous upper plate of the vertebra (caused by sclerotic changes etc.).

The first-mentioned inflammation can be overcome by suitable measures provided that the tissue in question is not permanently damaged.

In the latter case, the elevated pressure in the subchondral bone caused by the backing-up can, at least theoretically, result in mechanical irritation of the afferent nerve endings (mechanical pain). Measures bringing about a reduction in pressure in the subchondral region can at least reduce the mechanical pain if not cause it to disappear completely. However, the cause of the problem can be removed only with difficulty, even in the latter case.

Posterior displacement of the point of rotation to the region behind the posterior facet joints results in reduction of the load not only on the intervertebral disc but also on the subchondral bone located underneath. Accordingly, a suitable dynamic fixation creates the preconditions for the alleviation of pain and, in the case of inflammation in the region of the subchondral bone, even for healing.

6. Source of Pain: "Nerve Roots":

Mechanical pressure on the nerve roots results in numbness and muscle weakness radiating out into the lower extremities, but not in pain. Pain (ischialgia, etc.) occurs only when inflammation-triggering nuclear material emerges through tears in the posterior annulus and presses on the nerve roots.

In this case too, posterior displacement of the point of rotation of the spine segment reduces the subsequent flow of the nuclear material stimulating the inflammation process. As a result, the preconditions are created for healing of the inflammation and for the start of a certain repair process in the posterior annulus. It is even feasible to remove a disc hernia if there is no continuing flow of new nuclear material.

7. Problem: "Spinal Fracture":

In the case of a spinal fracture, it is usually the cranial vertebra of the segment concerned and the associated intervertebral disc that are affected. With the aid of good blood flow, bone healing of the vertebra no longer constitutes a problem with the fixation techniques described herein. Unlike the vertebra, healing of the intervertebral disc is, because of the lack of blood flow, subject to other rules and takes substantially longer. Changing from a rigid posterior fixation to a flexible posterior fixation after about 6 months brings about a reduction in the load on the intervertebral disc and allows certain flexibility of movement. Depending on the magnitude of the decrease in load and the remaining scope for movement, the preconditions are created for healing of the intervertebral disc provided that the supply to the intervertebral disc from the subchondral region of the adjacent vertebrae is not impeded (for example, as a result of callus formation in the region of the subchondral bone).

The posterior displacement of the point of rotation of the particular spine segment brought about in the case of a posteriorly implanted dynamic system brings about a reduction in the load on the injured intervertebral disc as already described hereinbefore and, in addition, allows axial deformation, which is important for the nutritional supply to the intervertebral disc.

In light of the above considerations, it is therefore also an aim, but not a requirement of the present invention, as a result of posterior displacement of the point of rotation of an affected spine segment, to immobilize the posterior annulus of the intervertebral disc concerned, with the consequence that posterior outflow of nuclear material is correspondingly reduced, whilst at the same time axial deformation, which is important for the nutritional supply to the intervertebral disc, should be possible, more specifically in such a manner that the intervertebral disc and the associated upper plates are subjected to pressure in a substantially homogeneous manner. Accordingly, it is also an objective of the present invention to make available a sufficiently dynamic stabilization system by means of which the point of rotation of the affected spine segment is displaced in a posterior direction in a predetermined manner.

Accordingly, the system should also preferably be distinguished firstly by an extremely elegant construction and operation technique and the advantages of a dynamic system, on the one hand, and by the possibility of optimum determination of the posterior point of rotation of a predetermined spine segment, on the other hand.

That problem preferably is solved by longitudinal member connecting means which preferably connects at least two longitudinal member portions.

From a medical point of view, it is preferable for the bone anchorage means, for example pedicle screws, that the connection between the bone anchorage means and the longitudinal member is polyaxial to guarantee stress-free implantation of the longitudinal member. After the implantation of the longitudinal member, said polyaxial connections can be lockable.

With respect to a viscoelastic longitudinal member, the load acting on the longitudinal member should be limited without compromising the strength of the locked polyaxial connection. This can be accomplished by having a load bearing means parallel to the longitudinal member which transfers a part of the load produced by the locking means directly to the clamping means locking the polyaxiality. For example, the load bearing means can be a fork engulfing the longitudinal member with a remaining distance "x" between the load bearing means and the clamping means. When the locking means is tightened, the resulting compression is initially taken up only by the viscoelastic longitudinal member causing a flattening of the longitudinal member. As soon as the deformation of the longitudinal member is equal to the distance "x", the additional compression will be directly transferred through the load bearing means to the clamping means locking the polyaxiality. The distance "x" depends on the mechanical characteristics of the viscoelastic longitudinal member.

A preferable embodiment of a polyaxial connection between the bone anchorage means and the viscoelastic longitudinal member is provided by a connecting element which can be clicked in situ onto the bone anchorage means with the polyaxiality preferably between the connector and the bone anchorage means. If a patient requires a revision surgery or conversion to fusion by replacing the viscoelastic longitudinal member by a metallic longitudinal member, the connector has only to be replaced by leaving the bone anchorage means in place.

Another preferred embodiment of a device is characterized in that the longitudinal member consists of a plastics rod, around which a metal wire, preferably a flat metal band, is helically wound. Preferably, the metal band is embedded in the plastics material. In a specific embodiment, the metal band is embedded in the plastics material in such a manner that it forms, together with the plastics material, a continuously smooth surface. The metal band can have interruptions, for example rows of holes, which are filled with plastics material.

Clamping of the longitudinal member constructed in such a manner is always carried out at locations reinforced, or covered, by the metal band. The longitudinal member is preferably in the form of a solid-construction plastics rod. However, it is also feasible for the longitudinal member to be in the form of a hollow rod or tube.

The metal band winding acts like an outer helical spring, giving the longitudinal member the requisite resilience in the particular deformed state, more particularly a resilience which exceeds that which is intrinsic to the plastics rod.

When the diameter of the longitudinal member is about 6.0 to 8.0 mm, the width of the metal band is about 4.0 to 6.0 mm. The afore-mentioned interruptions may then have a diameter of about 2.0 to 3.0 mm.

If the longitudinal member is in the form of a hollow rod or tube, the wall thickness is about 1.5 to 2.0 mm, preferably about 1.5 mm.

In a specific embodiment, the winding of the metal band around the plastics rod is tightly spaced so that the axial spacing between neighboring turns of metal band is only about 1.5 to 3.0 mm. The winding of the metal band is carried out at an angle of about 15° to 30° relative to the plane extending perpendicular to the longitudinal axis of the longitudinal member, or cross-sectional plane. The metal band may consist of titanium or titanium alloy and has a thickness of about 0.2 to 0.4 mm, of course that being dependent, in the final analysis, on the overall dimensions of the longitudinal member.

The end-face extremities of the longitudinal member are preferably metal caps or metal discs. Those end-face metal caps or metal discs can also be connected to one another by means of a wire passing centrally through the longitudinal member, more specifically in such a manner that the end-face metal caps or metal discs can be tensioned with respect to one another in an axial direction. For that purpose, the central metal wire extends through the metal caps or metal discs, more specifically in such a manner that it projects outwards at the end faces as projecting portions, each of those projecting portions having a screw thread so that tensioning nuts can be screwed onto the central metal wire from the outside.

In an alternative embodiment, the longitudinal member is also a plastics rod in which a metal armoring has been embedded. That metal armoring can be constructed in numerous different ways.

In a preferred embodiment, there is provided a device for dynamic stabilization of bones or bone fragments comprising: at least one anchor member for attachment to vertebrae having an opening configured to receive a longitudinal member; and the longitudinal member being viscoelastically deformable and having a predetermined bending resilience comprising a biocompatible plastics material, whereby the plastics material provides for viscous deformability, and a biocompatible metal, whereby the metal provides for resiliently flexible deformability.

There is also provided a device for dynamic stabilization of bones or bone fragments comprising: at least one anchor member for attachment to vertebrae having an opening configured to receive a longitudinal member; and the longitudinal member being viscoelastically deformable and having a predetermined bending resilience comprising a plastic rod comprising biocompatible plastics material in which metal armoring comprising biocompatible metal is embedded.

There is also provided a device for dynamic stabilization of bones or bone fragments comprising: at least one anchor member for attachment to vertebrae having an opening configured to receive a longitudinal member; the longitudinal member being viscoelastically deformable and having a predetermined bending resilience comprising a biocompatible plastics material, whereby the plastics material provides for viscous deformability, and a biocompatible metal, whereby the metal provides for resiliently flexible deformability; and metal armoring comprising at least three metal rods extending parallel to the longitudinal member.

There is also provided a device for dynamic stabilization of bones or bone fragments comprising: at least one anchor member for attachment to vertebrae having an opening configured to receive a longitudinal member; and the longitudinal member being viscoelastically deformable and having a predetermined bending resilience comprising a biocompatible plastics material, whereby the plastics material provides for viscous deformability, a biocompatible metal, whereby the metal provides for resiliently flexible deformability; and at least a portion of the metal forms a continuous spiral.

BRIEF DESCRIPTION OF THE DRAWINGS

Corresponding examples embodying a stabilization system will be explained hereinbelow in greater detail with reference to the accompanying exemplary and illustrative drawings. The drawings are merely exemplary to illustrate the structure of devices and features that may be used singularly or in combination with other features and structures. The invention should not be considered limited to the embodiments shown.

FIG. 19A is a diagrammatic side view of a thirteenth embodiment of a longitudinal member contained within diagrammatic cross section of anchoring members;

FIG. 19B is a diagrammatic side view of the embodiment of FIG. 19A of a longitudinal member contained within diagrammatic cross section of anchoring members;

FIG. 19C is a diagrammatic side view of the embodiment of FIG. 19A of a longitudinal member contained within diagrammatic cross section of anchoring members;

FIG. 20A is a diagrammatic side view of a fourteenth embodiment of a longitudinal member contained within diagrammatic cross section of anchoring members, configured for a two level stabilization, the longitudinal member contained within a diagrammatic cross-section of three anchor members;

FIG. 20B is a diagrammatic side view of the embodiment of FIG. 20A of a longitudinal member contained within diagrammatic cross section of anchoring members, configured for a two level stabilization, the longitudinal member contained within a diagrammatic cross-section of three anchor members;

FIG. 20C is a diagrammatic side view of the embodiment of FIG. 20A of a longitudinal member contained within diagrammatic cross section of anchoring members, configured for a two level stabilization, the longitudinal member contained within a diagrammatic cross-section of three anchor members.

DETAILED DESCRIPTION OF THE INVENTION

Figure 1:
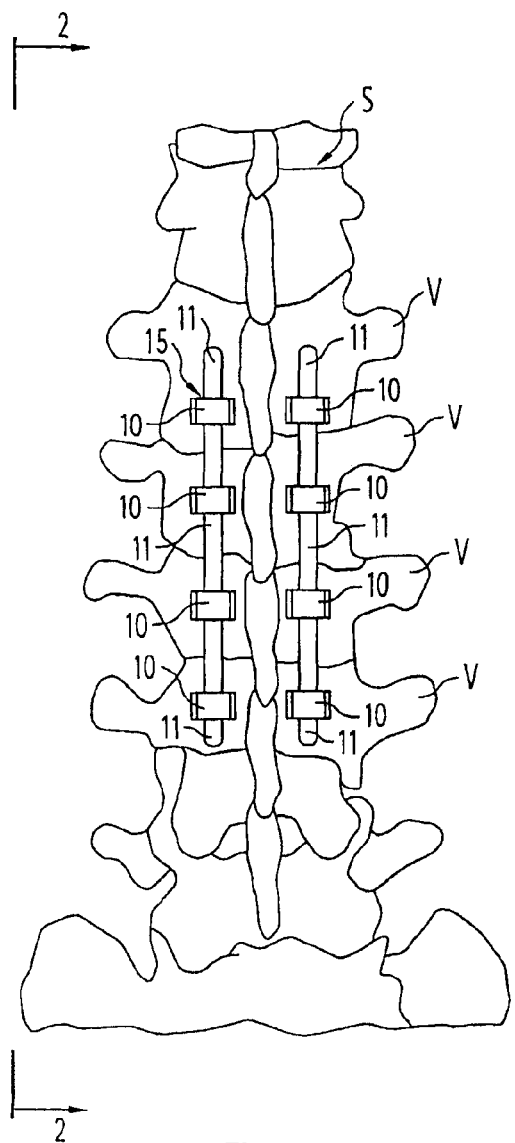
FIG. 1 is a view from the posterior direction of a spine segment comprising four vertebrae, with posterior stabilization of that segment.
Figure 2:
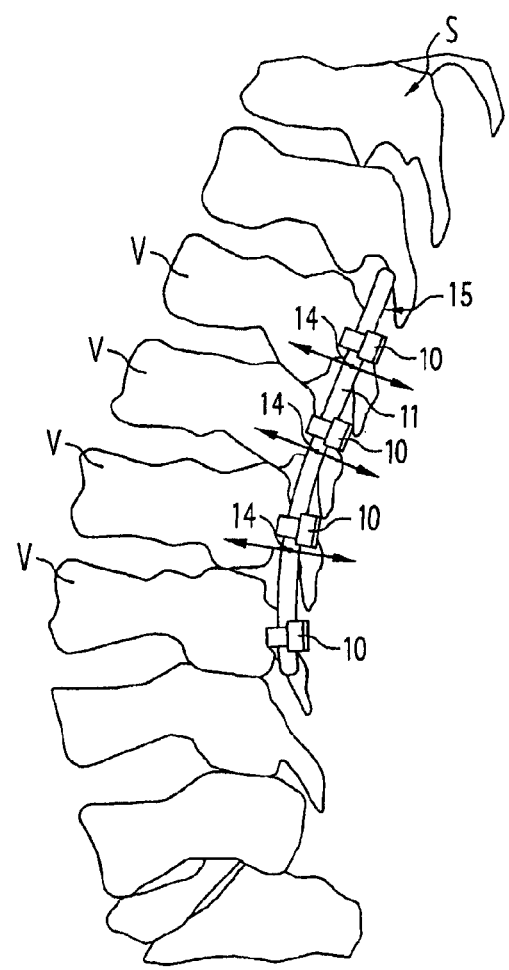
FIG. 2 is a side view along line 2-2 according to FIG. 1 of the arrangement according to FIG. 1.

FIGS. 1 and 2 show part of a spine, reference letter "V" denoting the individual vertebra. Reference letter "S" denotes the spine. While the stabilization system is shown and described with reference to its use for spiral applications, it is understood and contemplated that the stabilization system may have applications in other areas of the body and in animals.

The individual vertebra "V" have been stabilized posteriorly; more specifically, for that purpose pedicle screws have been screwed into four vertebrae "V" from the posterior direction. The heads of the screws 10 each have accommodation apertures or accommodation slots or openings for accommodating a rod-shaped longitudinal member 11. The longitudinal member 11 is, as can be seen especially from the further figures, of generally round rod-shaped construction and is fixed by clamping in the heads of the pedicle screws 10. In that manner, a spine segment having four vertebrae "V" can be stabilized. The longitudinal member or members 11 are so designed that they are plastically deformable, by application of a predetermined bending force, from a first stable shape state to a second, alternative stable shape state in accordance with FIGS. 1 and 2. However, within that implantation state, the longitudinal members 11 should be resiliently or elastically flexible, more specifically within predetermined limits as described above. As a result, dynamic stabilization of a predetermined spine segment is achieved preferably with all the advantages mentioned hereinbefore. The aforementioned bending resilience of the longitudinal member(s) 11 is indicated in FIG. 2 by a double-headed arrow 14 and is so dimensioned that, in situ, when the longitudinal member 11 is held at one extremity, it can be resiliently deflected, within a dimensionally stable state, about an angle of about 8° (double-headed arrow 14). Accordingly, flexion in the sagittal plane is provided.

It should be mentioned again at this point that the described device can comprise longitudinal member connecting means, by means of which at least two longitudinal member portions can be connected to one another. The longitudinal member connecting means can have, for example, two longitudinal member accommodation apertures or accommodation slots or openings located opposite one another, into each of which one longitudinal member end portion can be inserted and, by means of a clamping screw or the like, fixed. The longitudinal member connecting means may be a pedicle screw, such as, for example, a monoaxial or polyaxial pedicle screw, or hook, or other device and mechanism for attaching the longitudinal member to one or more vertebrae.

The longitudinal member connecting means can be either of rigid or, preferably, of resiliently flexible construction. They preferably allow segment-wise implantation of longitudinal members and highly individual stabilization of a portion of spine.

From FIGS. 1 and 2 it can otherwise also be seen that stabilization of a portion of spine by means of the device is carried out that flexibility is present only in respect of flexion and extension. As a result, pressure on the upper plate and intervertebral disc is considerably reduced without losing axial deformation of the intervertebral disc, which is important for the nutritional supply thereof. The described longitudinal member also is preferably constructed that it can be lastingly deformed using a predetermined force which exceeds anatomical or in vivo peak forces. That deformation is carried out outside of the implantation; it should preferably be possible without special ancillary apparatus. Deformation is accordingly carried out "on site" by the operating surgeon.

Both in the longitudinal direction of the longitudinal member and also in the direction transverse thereto, the longitudinal member should be stable, that is to say unyielding, with respect to anatomically shear forces usually present in vivo. In addition, it is very often desirable for the longitudinal member to be torsion-resistant in order to ensure that extension of the vertebral segment concerned generally occurs substantially only about a posteriorly displaced point of rotation approximately horizontal. As already mentioned hereinbefore, the longitudinal member can be in the form of a flat band or strip. In the embodiments described, longitudinal members in the shape of round rods are implanted.

With respect to the bending resilience, it should also be mentioned that the angular range mentioned hereinbefore is based on a length of the longitudinal member 11 which corresponds to the spacing between two neighboring vertebrae, that is to say a spacing of about 2 cm to about 6 cm, especially about 4 cm to about 5 cm.

Reference numeral 15 denotes the entire stabilization system shown in FIGS. 1 and 2.

Figure 3:
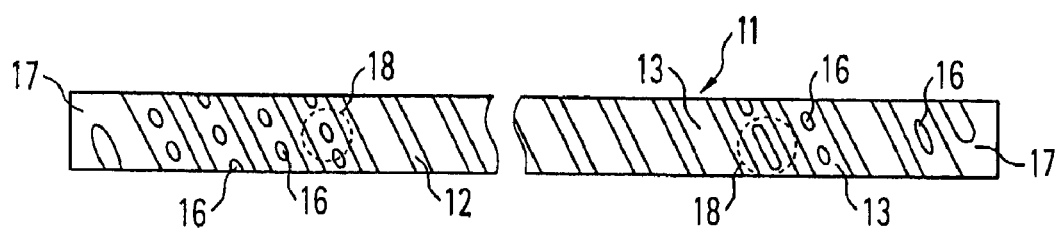
FIG. 3 is a diagrammatic side view of a first embodiment of a longitudinal member.

In the case of the embodiment according to FIG. 3, the longitudinal member 11 consists of a plastics rod 12, around which a flat metal band 13 is helically wound. The metal band 13 is embedded in the plastics material of the rod 12, more specifically in such a manner that, together with the plastics material, it forms a continuously smooth surface. The metal band moreover has interruptions 16 in the shape of circles or elongate holes, which are likewise filled with plastics material so that a substantially smooth surface of the rod-shaped longitudinal member 11 is produced. With respect to preferred dimensions for a longitudinal member of such a kind, reference is made to the statements hereinbefore.

The end-face extremities of the longitudinal member 11 can be, and preferably are, limited by metal caps or metal discs. In the embodiment according to FIG. 3, the end-face limitation is defined by metal caps 17 out from which the helical sheathing of the plastics-comprising rod 12 is then developed.

The plastics rod 12 can also be tube- or tubule-shaped, that is to say hollow. The end faces are closed off by metallic discs or plugs. In the final analysis, the embodiment of the plastics rod is dependent on the application area and also on the requisite dimensional stability and flexibility of the longitudinal member.

Reference numeral 18 denotes the clamping sites of the longitudinal member 11 in FIG. 3. Accordingly, the longitudinal member 11 is clamped in the region of the metallic sheathing. As a result it is possible to avoid the plastics material retreating or "creeping away" under the pressure of a clamping screw after a relatively long period of use. Because the winding of the metal band 13 on the plastics rod 12 is very tightly spaced, the longitudinal member 11 according to FIG. 3 can be clamped at practically any location.

The embodiments of FIGS. 4-9 are all characterized in that the longitudinal member consists of a plastics rod 12 in which metal armoring is embedded. The latter can be, for example, in the form of a round or flat profile having a meandering curve shape, the meandering curves preferably extending to the peripheral surface of the longitudinal member 11, which otherwise consists of plastics material. In the case of the embodiment according to FIG. 4, the metal armoring is formed by a flat profile 19, which is defined by one or more "V"-shaped or "W"-shaped elements 20 alternately rotated 180° and connected together. Each of the "V"-shaped or "W"-shaped elements 20 extends to the peripheral surface of the longitudinal member 11, which otherwise consists of plastics material, with those parts of the armoring which reach the surface, in conformity with the peripheral surface of the longitudinal member 11, each being rounded in accordance with the cross-sectional periphery of the longitudinal member.

Figure 4:
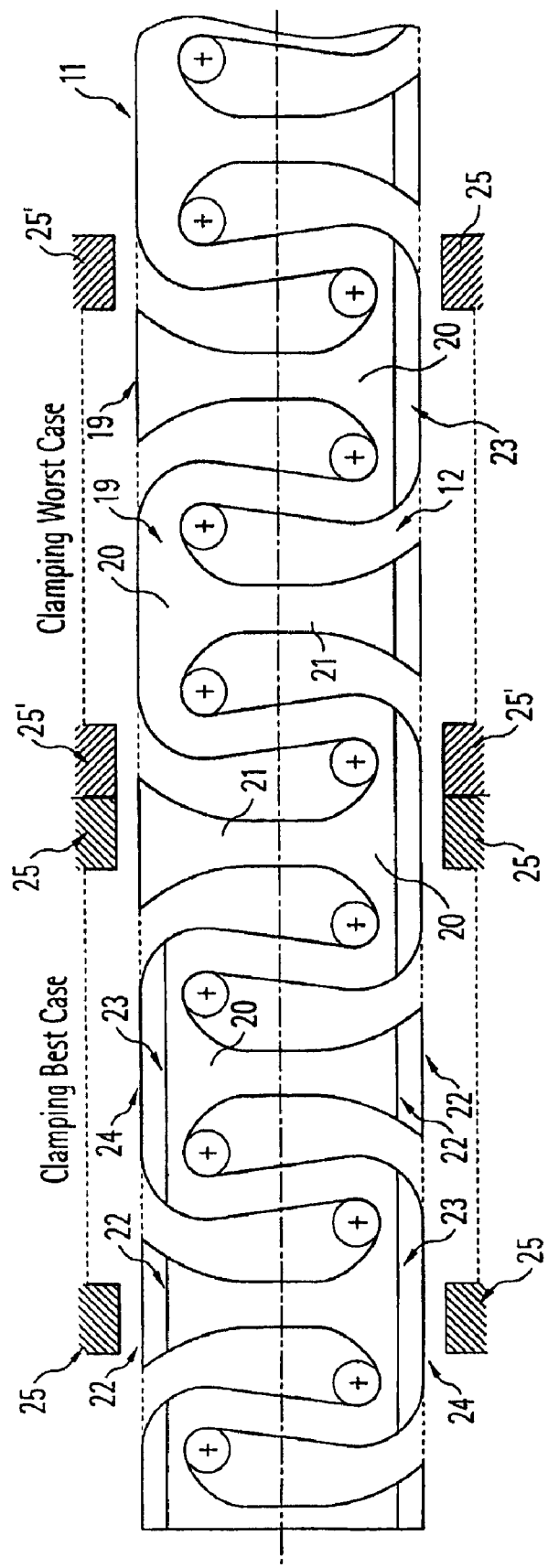
FIG. 4 is a diagrammatic side view of a second embodiment of a longitudinal member.

The central members 21 of the "V"-shaped or "W"-shaped elements 20 are widened both in the longitudinal direction and in the transverse direction to form support surfaces 22, which are rounded off in the direction transverse to the longitudinal axis of the longitudinal member 11 and integrated flush into the peripheral surface 24 of the longitudinal member 11. The outer surfaces 23 of the connecting members 24 of the "V"-shaped or "W"-shaped elements 20 are likewise rounded off in each case in the direction transverse to the longitudinal axis of the longitudinal member 11 so that they can be integrated flush into the peripheral surface of the longitudinal member 11. The longitudinal member 11 according to FIG. 4 is clamped or fixed at the metal surfaces of the central member 21 and connecting member 24, which are flush with the peripheral surface of the longitudinal member 11. In that regard, FIG. 4 shows, in diagrammatic manner, on the one hand, the so-called "best case" and, on the other hand, the "worst case". The "best case" situation is indicated in FIG. 4 by the clamps 25. The "worst case" situation corresponds to the relative position of the clamps 25' in FIG. 4.

Figure 21:
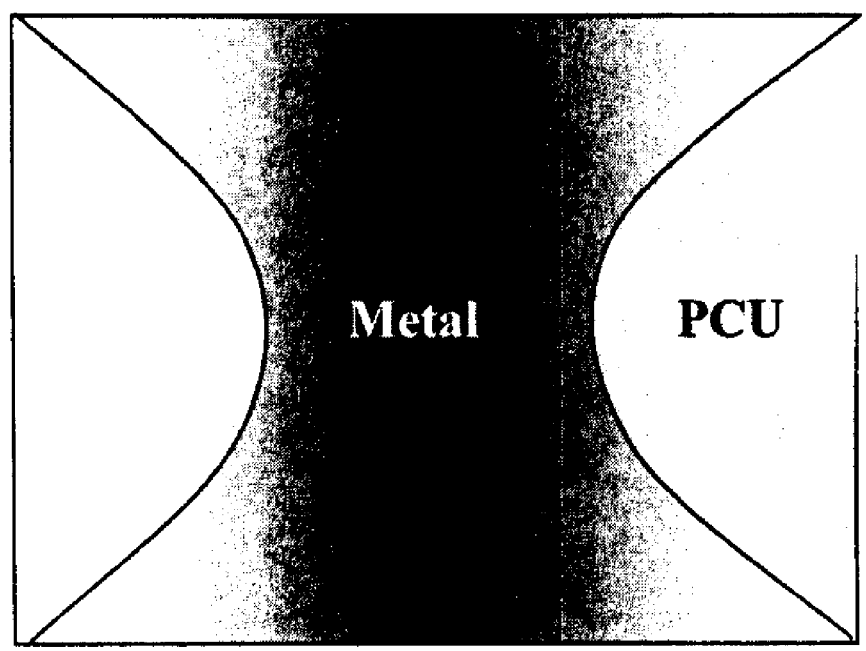
FIG. 21 is a graphic representation of a waisted cross-section.

Otherwise, the flat profile 19 is constructed with a waisted cross-section as depicted in FIG. 21. The metal portion may be formed similar to an "I" beam as shown, or similar to a "C"-shape (not shown) if FIG. 21 is bisected. The plastic material may be on one or both sides of the middle columnar support of the "I" beam or "C"-shaped element.

In the plane of the sheet of the drawing, the metal armoring 19 according to FIG. 4 is relatively flexible, or resilient in flexion. In the plane perpendicular to the sheet of the drawing, the flat profile 19 is relatively rigid. Accordingly, therefore, there is a preferred plane of deformation, which has to be taken into account on implantation.

Figure 6:
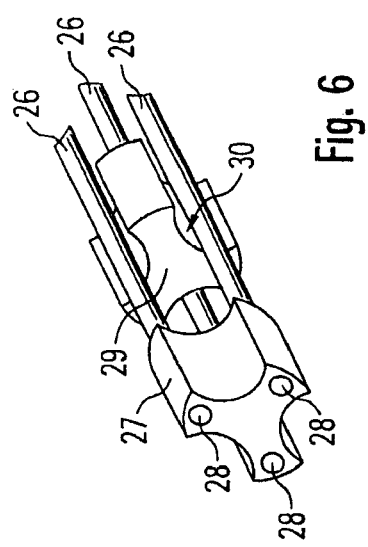
FIG. 6 is a perspective view of an end-face end portion of a metal armoring of the longitudinal member according to FIG. 5.
Figure 5:
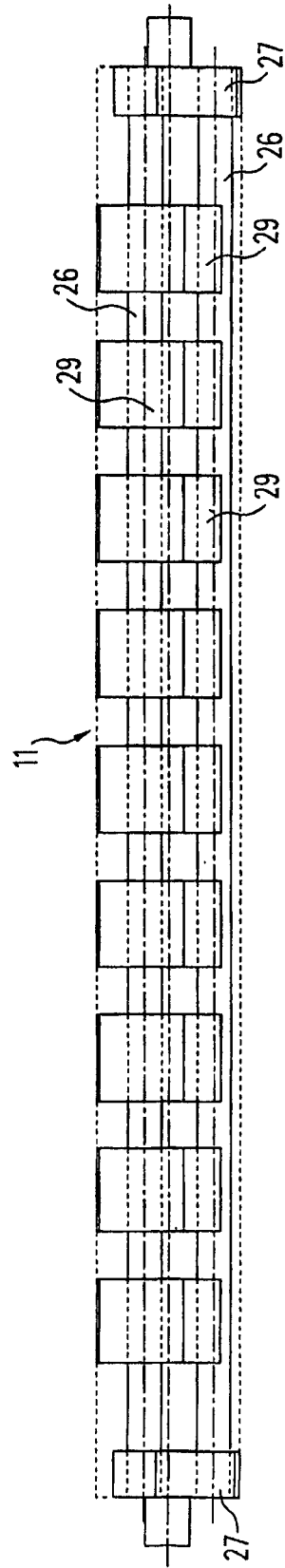
FIG. 5 is a diagrammatic side view of a third embodiment of a longitudinal member.

In the case of the embodiment according to FIGS. 5 and 6, the metal armoring comprises three metal rods 26, which extend parallel to the longitudinal direction of the longitudinal member 11 and at the same angular spacing from one another (see FIG. 6) and which are fixed at the end faces through star-shaped discs 27, especially being shrunk into corresponding through-holes. In FIG. 6, reference numeral 28 denotes those through-holes.

Held between the three metal rods 26 are a plurality of disc-shaped supporting elements 29, each of which extends to the peripheral surface of the longitudinal member 11, which otherwise consists of plastics material. The supporting elements 29 are spaced apart from one another in the axial direction, and, in particular, preferably spaced apart equally from one another. The intermediate space is filled by plastics material. The longitudinal member 11 is a round rod of biocompatible high-performance plastics material, for example PCU, having armoring in accordance with FIGS. 5 and 6. The disc-shaped supporting elements 29 have, at their edges, three recesses 30, through which the metal rods 26 extend. The three recesses 30 are each arranged uniformly around the periphery of the supporting discs 29.

The metal rods 26, embedded in the plastics material, each extend close to the peripheral surface of the longitudinal member 11. In this case too, the metal rods serve to ensure the bending resilience in a predetermined stable shape state of the longitudinal member 11. For better anchorage between the plastics material and metal it is also feasible for the surface of the metal rods 26 to be roughened.

Figure 7:
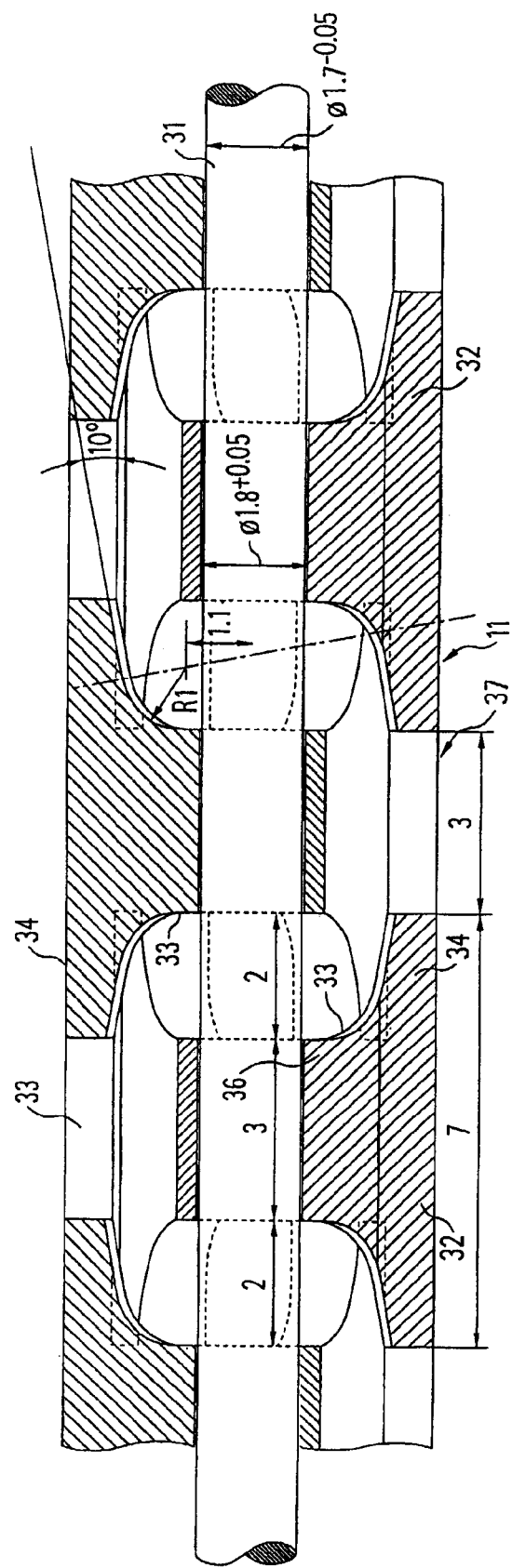
FIG. 7 is a longitudinal section through part of a fourth embodiment of a longitudinal member.
Figure 8:
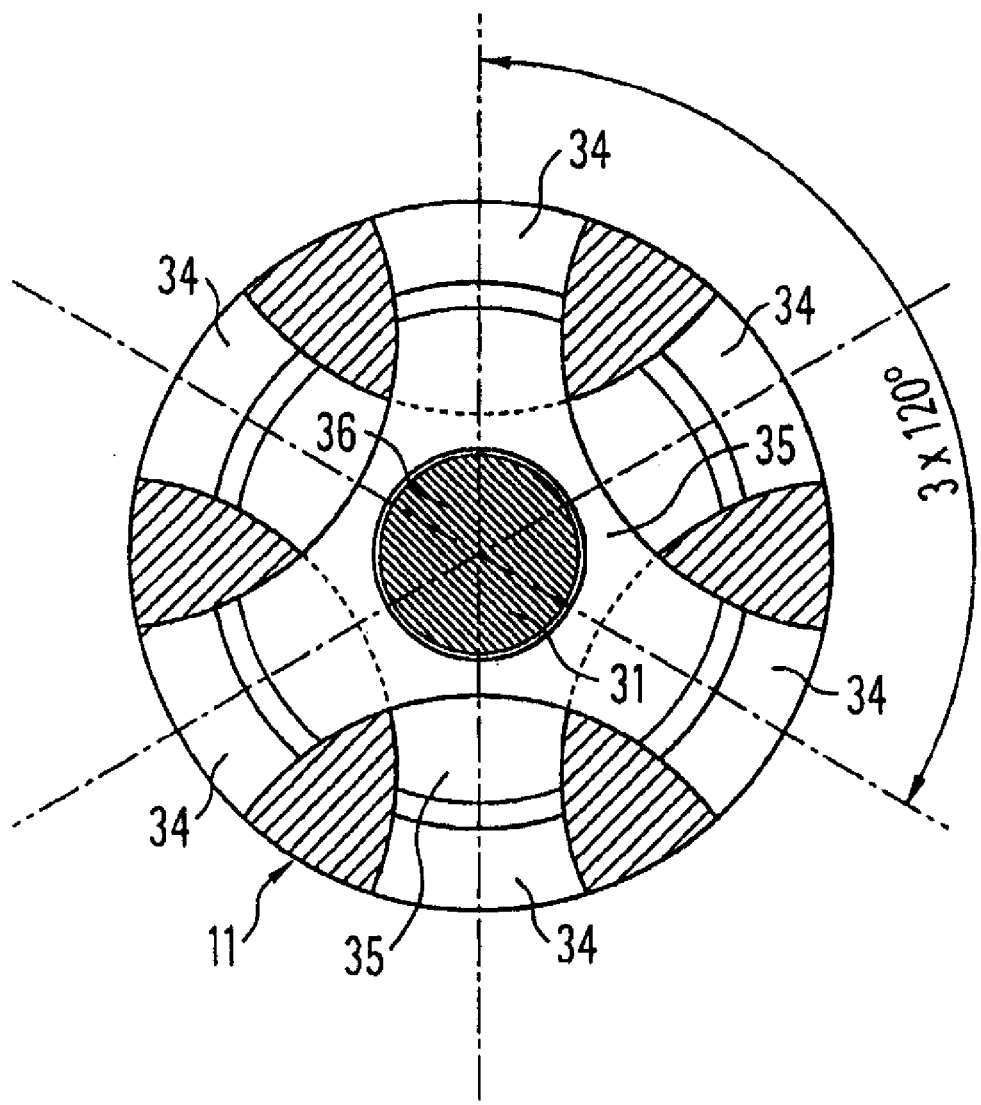
FIG. 8 is a diagrammatic cross-section through the embodiment according to FIG. 7.

The embodiment according to FIGS. 7 and 8 is characterized in that the metal armoring comprises at least one central metal rod 31, which extends parallel to the longitudinal direction of the longitudinal member 11 and on which metal sleeves 32 are mounted. The metal sleeves may comprise a hub having longitudinal elements 34 extending therefrom. Longitudinal recesses 33 separate the longitudinal elements 34. The metal sleeves 32 have at their end faces respectively facing one another longitudinal recesses 33, in this case three, arranged uniformly around the periphery, into which recesses 33, longitudinal elements 34 formed there between of a directly neighboring metal sleeve 32 can be inserted so that neighboring metal sleeves 32 can, if required, be pushed into one another, offset at an angle to one another, on the at least one metal rod 31, as shown in FIG. 7. The angular offset between neighboring metal sleeves can be seen more clearly from FIG. 8.

Between the end-face longitudinal recesses 33 of the metal sleeves 32, spaced away from the free extremity, the longitudinal elements 34 are connected to one another by a central, preferably star-like, connecting element 35, the connecting element 35 having a central longitudinal hole 36 for accommodation of the central rod 31, on which the metal sleeve or sleeves 32 can be mounted. The metal sleeves 32 accordingly form, in the region of end faces inserted into one another, a kind of articulated connection 37, which allows bending of the longitudinal member 11 within predetermined limits.

The external diameter of the metal sleeves 32 otherwise corresponds to the external diameter of the plastics portion of the longitudinal member 11. The sleeves 32 are embedded in the plastics material. Preferably, however, the external diameter of the metal sleeves 32 corresponds to the external diameter of the plastics-comprising longitudinal member 11 so that the external peripheral surfaces of the metal sleeves 32 and longitudinal elements 34 are an integral part of the peripheral surface of the longitudinal member 11. The longitudinal member 11 according to FIGS. 7 and 8 can be lastingly fixed, that is to say firmly clamped, in the region of those metal sleeves, preferably directly next to an articulated connection.

Figure 9:
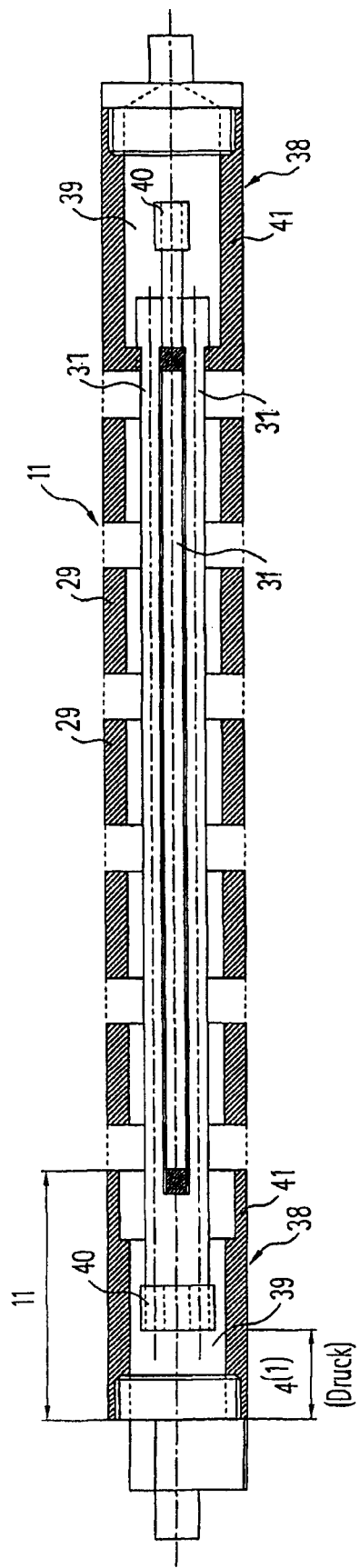
FIG. 9 is a diagrammatic longitudinal section through a fifth embodiment of a longitudinal member.

FIG. 9 shows a fifth embodiment of a longitudinal member, wherein the metal armoring comprises three metal rods 31 extending parallel to the longitudinal direction of the longitudinal member 11, one of the extremities of two of the metal rods 31 being fixed, especially welded, to one of the two end-face end caps 38, more specifically the right-hand end cap 38 in FIG. 9, whilst the other, in that case free, extremity of each is embedded in the plastics material 39. The third rod 31, namely the middle rod in FIG. 9, is fixed to the other end cap 38, namely the left-hand end cap 38 in FIG. 9. The right-hand, free extremity of that third metal rod is, in contrast, accommodated, floating, in the plastics material 39. The free extremities of the metal rods 31 each have a thickened portion 40, the thickened portions of the upper and lower metal rods 31 in FIG. 9 being formed to make a connection of the free extremities of those two metal rods. The thickened portion 40 promotes embedding in the plastics material and the clamping action of the latter on resilient deformation of the longitudinal member 11. In this context it is to be noted that the longitudinal member according to the invention is constructed according to the so-called Kelvin-Voigt model. The longitudinal members 11 shown constitute a modified Kelvin-Voigt model, in particular having a serially appended resilient element (spring element).

Otherwise it can be seen from FIG. 9 that the respective free extremities of the metal rods 38 are embedded in the plastics material 39 within sleeve-like portions 41 of the end-face end caps 38 of the longitudinal member 11.

It should also be mentioned that the end-face end caps 38 in FIG. 9, or 27 in FIG. 6, of the longitudinal member 11 can be tensioned with respect to one another in the axial direction.

In the embodiments shown, the metal rods described herein (e.g., 26 in FIGS. 5 and 6; 31 in FIG. 7; and 38 in FIG. 9) each have a constant diameter over their length. However, it is feasible for the diameter to vary over the length, for example decreasing or increasing continuously or in stepwise manner towards the middle of the longitudinal member 11 or vice-versa.

Otherwise it should also be mentioned in respect of FIG. 9 that between the two end caps of the metal rods 31 there are held supporting elements 29 corresponding to those described in connection with FIGS. 5 and 6. Clamping of the longitudinal member 11 can take place at those supporting elements 29, and also in the region of the end caps 38, without there being a risk of that clamping becoming loose after a relatively long period of use. The supporting elements 29 also have the function of metal wire spacer elements, that is to say they keep the metal wires at a constant spacing from one another over their length. That spacing is maintained even after plastic deformation of the longitudinal member 11. As a result, a defined "flexing" of the longitudinal member is also obtained after deformation thereof.

In addition to its viscous deformation property, the biocompatible high-performance plastics material used herein also preferably has the property of having a shock-absorbing action.

It should also be mentioned that it is desirable for the plastics material to prevent the formation of openings in the longitudinal member into which tissue could grow. The longitudinal member 11 is, in the case of all the embodiments described, is preferably a round rod having a smooth surface. The plastics material used is preferably transparent so that the metal armoring is visible. As a result it can also be seen at which sites the longitudinal member 11 can be tightly clamped.

Figure 10:
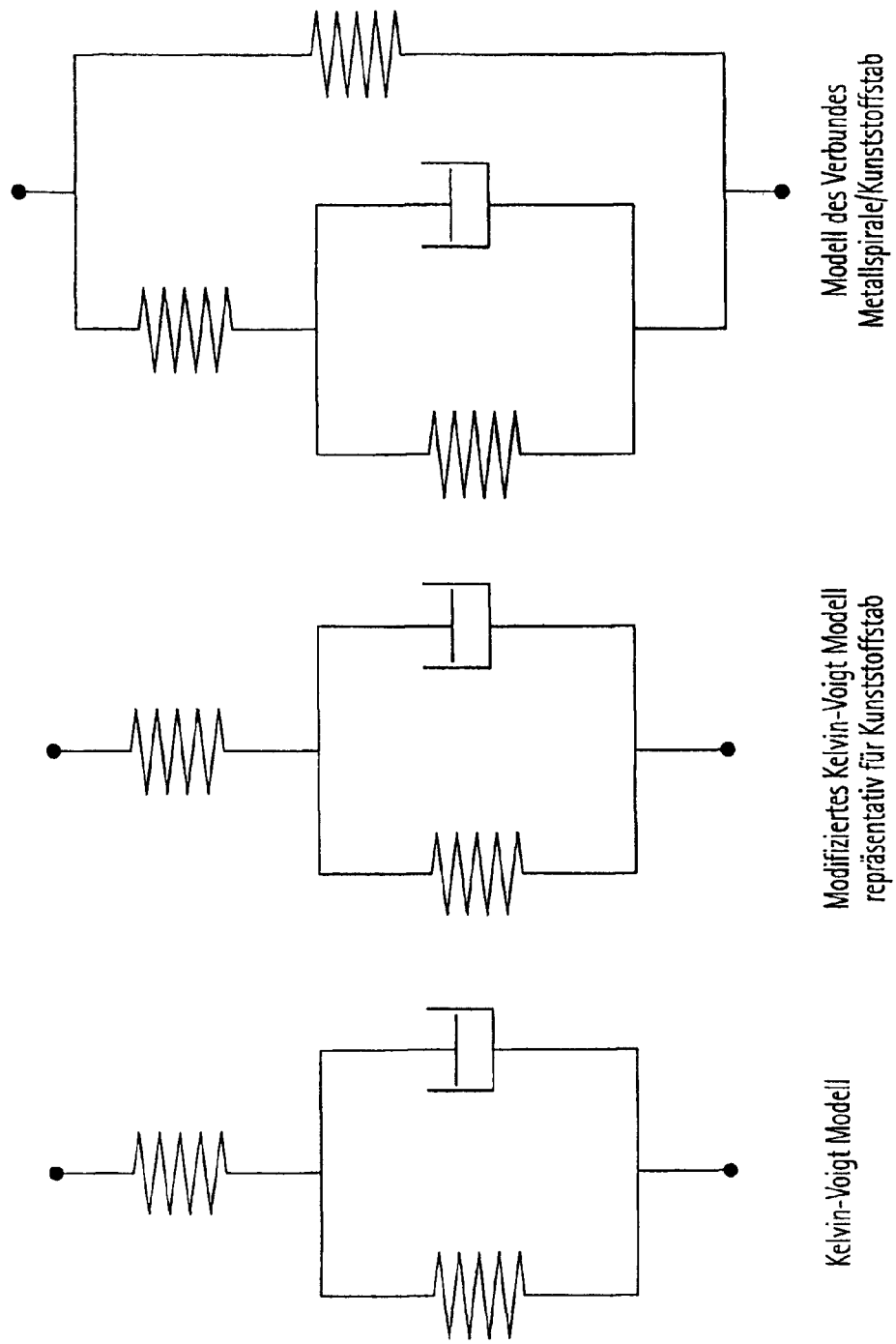
FIG. 10 is a model view for the stabilization system of FIG. 3, which also applies in corresponding manner to the other embodiments.

FIG. 10 shows the fundamental difference between the system according to the invention (the right-hand illustration in FIG. 10) and the prior art (the left-hand and middle illustrations in FIG. 10) using the so-called Kelvin-Voigt model. In the case of the prior art according to the left-hand illustration in FIG. 10, the longitudinal member or connecting rod consists of, for example, titanium or a titanium alloy. Such a rod comprises both a flexing or spring component and also a clamping component, with both components being in parallel connection with respect to one another. When, instead of titanium or the like, plastics material, for example PCU, is used, a further flexing component is added in series to the two afore-mentioned components (middle illustration in FIG. 10). In accordance with the invention, yet another flexing component is introduced, in parallel, to the last-mentioned model (right-hand illustration in FIG. 10).

This last-mentioned model very clearly represents the "recoiling" effect that is desirable for the composite. The spring in each of the two Kelvin-Voigt models according to the left-hand and middle illustrations of FIG. 10 in parallel connection to the clamper does, of course, also result in a certain "recoiling" effect. According to mechanical tests with PCU material, that effect is relatively slow. Recovery of the PCU material takes several hours. By means of the metal component in parallel connection to the PCU material, for example the metal spiral according to FIG. 3, the "recoiling" effect of the PCU material can be accelerated to a greater or lesser degree depending on the material selected and on the geometry of the metal component.

Figure 11:
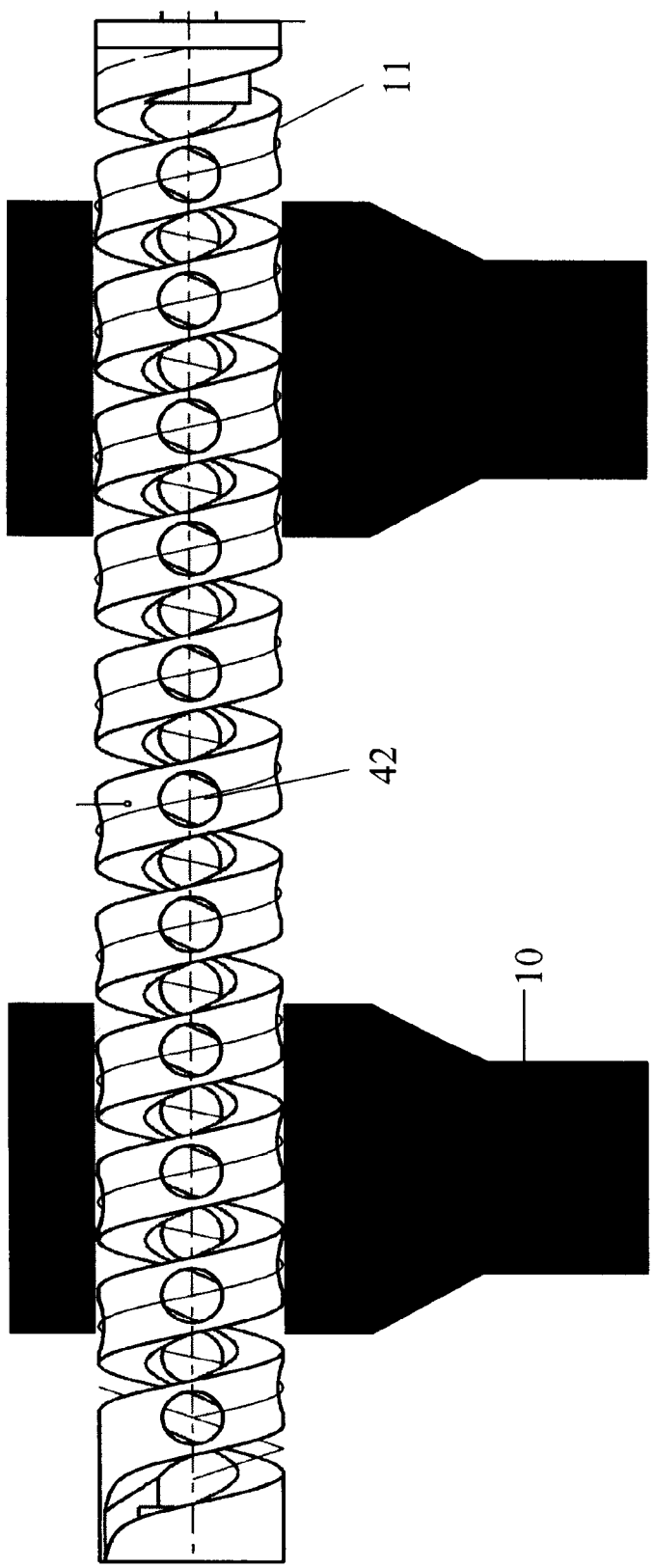
FIG. 11 is a diagrammatic side view of a fifth embodiment of a longitudinal member contained within diagrammatic cross section of anchoring members.
Figure 12:
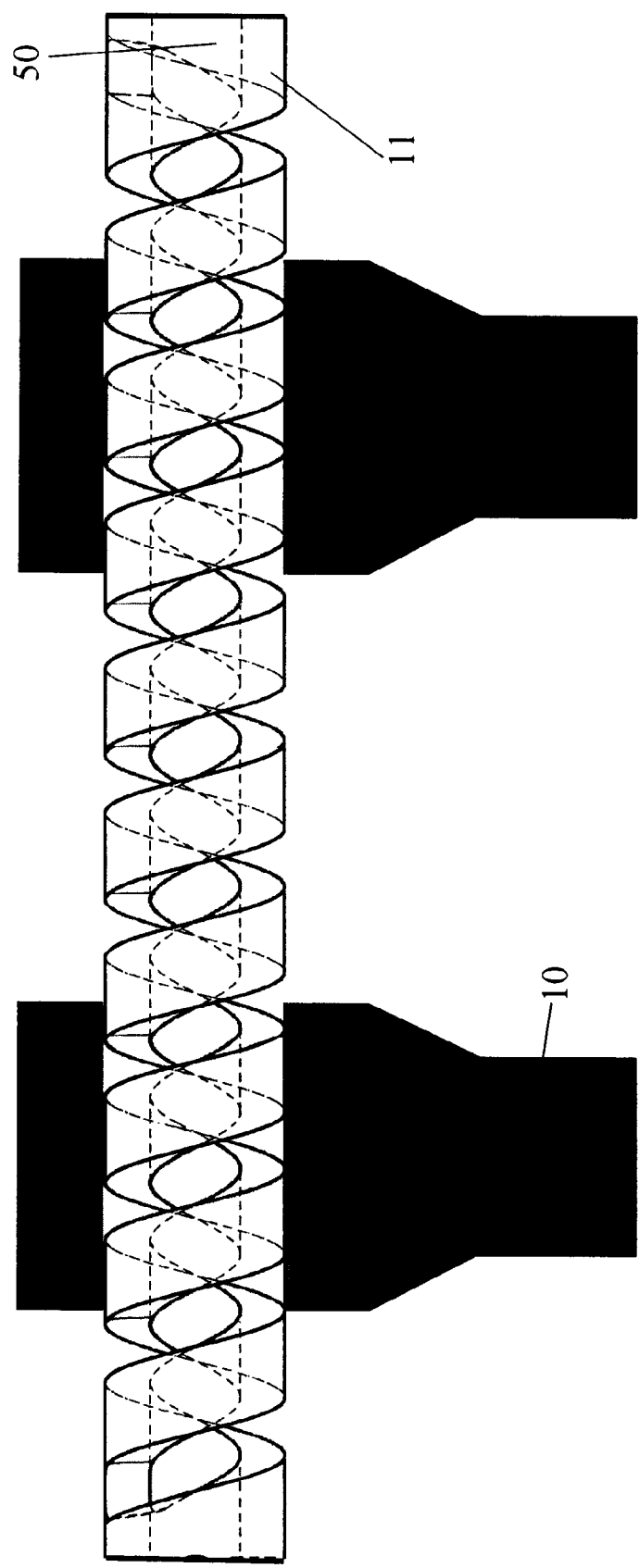
FIG. 12 is a diagrammatic side view of a sixth embodiment of a longitudinal member contained within a diagrammatic cross section of anchoring members.

In the embodiment according to FIGS. 11 and 12, the longitudinal member 11 consists of a continuous spiral of biocompatible metal such that the resulting structure is tube- or tubule-shaped, having a hollow cavity 50 in the center. The wire forming the spiral may be round or preferably flat ribbon wire. Because the longitudinal member is fairly homogenous along its length (e.g., a continuous spiral structure), the position of the pedicle screws 10 can be located anywhere along the length of the spiral longitudinal member. The longitudinal member preferably has the same diameter throughout the structure which promotes percutaneous application of the longitudinal member.

The hollow spiral longitudinal member can be filled with biocompatible plastics material, for example PCU. The plastics material can fill the gaps of the spiral wire as well as the hollow core of the spiral. The spiral wire may be flush with the plastics material at the perimeter of the longitudinal member, or may only fill the hollow cavity 50, or may only partially fill the gaps between the spiral wire. The spiral wire filled with biocompatible plastics material provides resistance to collapse in the area of the pedicle screw and an overall resistance to buckling. The plastics material filling the gaps of the spiral provides a larger stiffness in compression. Only the core portion of the plastics material contributes to the resistance in the tension since the metal spirals are separated by the plastics material in between the gaps of the spiral.

The longitudinal member can also consist of cross holes 42, which can be used for anchorage of the biocompatible plastics material, as depicted in FIG. 11. The cross holes may provide relative movement between the metal spiral and the biocompatible plastics material filling. The spiral longitudinal member can be locked in the pedicle screws 10 using a clamping mechanism as described above.

Figure 13:
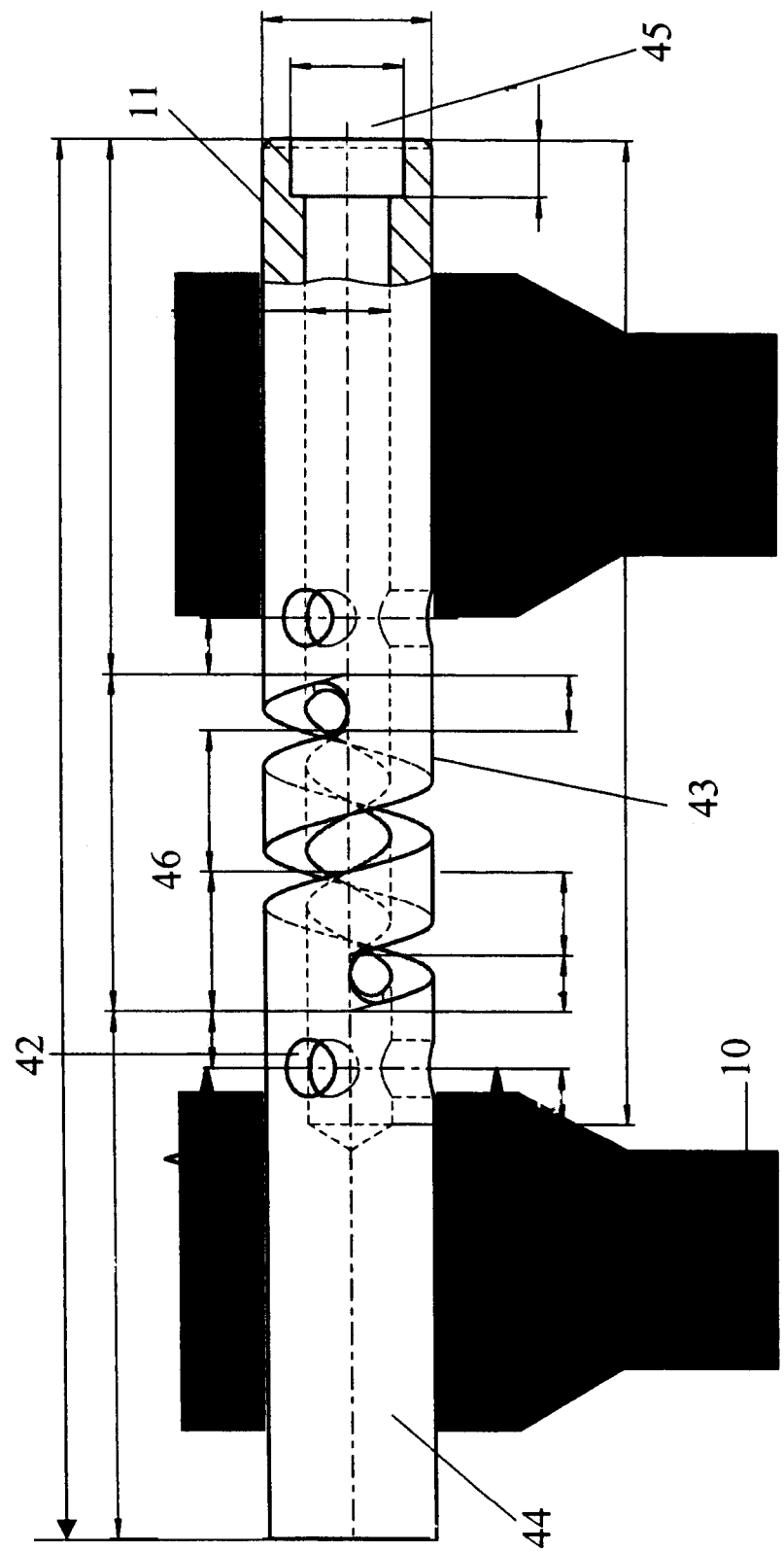
FIG. 13 is a diagrammatic side view of a seventh embodiment of a longitudinal member contained within diagrammatic cross section of anchoring members.
Figure 14:
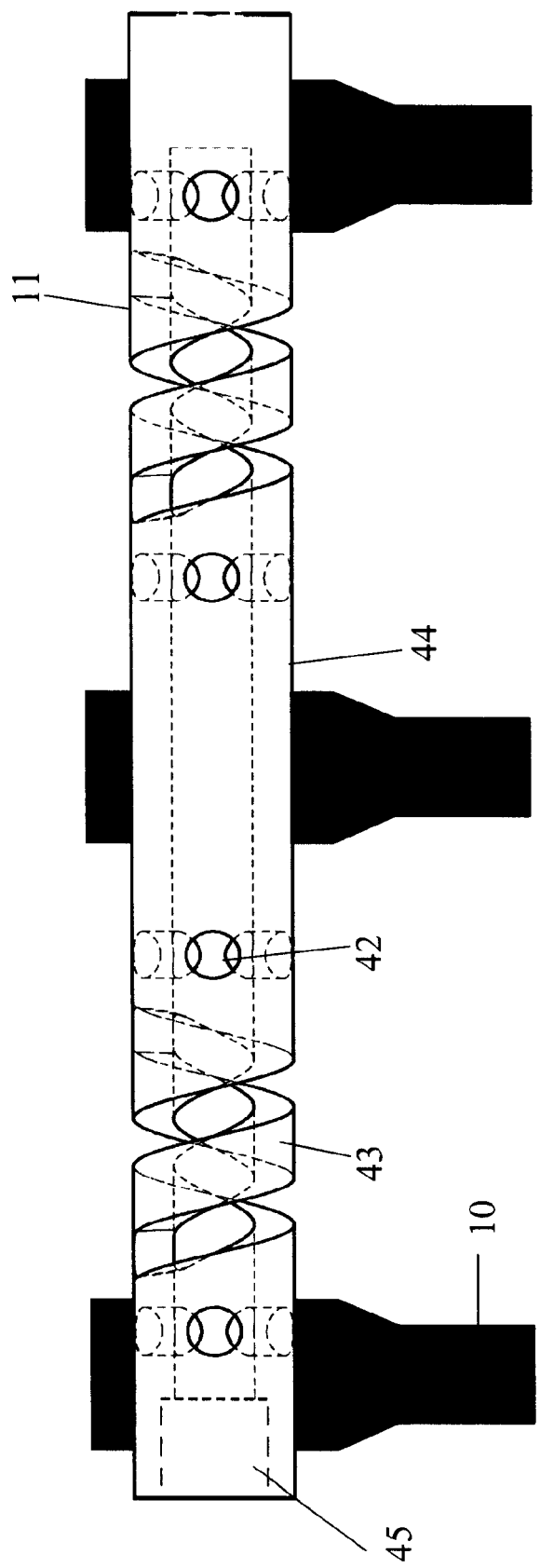
FIG. 14 is a diagrammatic side view of an eighth embodiment of a longitudinal member, similar to the longitudinal member of FIG. 13, but configured for a two level stabilization, the longitudinal member contained within three anchoring members.

In the embodiment according to FIGS. 13 and 14, the longitudinal member 11 consists of alternating non-spiral portion 44 and spiral portion 43. The spiral portion 43 is structured as described above for the embodiments of FIGS. 11 and 12. The non-spiral portion 44 of the longitudinal member can be structured as described for prior embodiments above. Because the longitudinal member is non-homogenous along its length (e.g., alternating non-spiral and spiral portions), the position of the pedicle screws 10 along the length of the longitudinal member has preferred locations. The pedicle screws 10 preferably are positioned outside of the spiral portion 43 and can be compatible with any pedicle screw system, thus no special clamping mechanism may be required.

Figure 15:
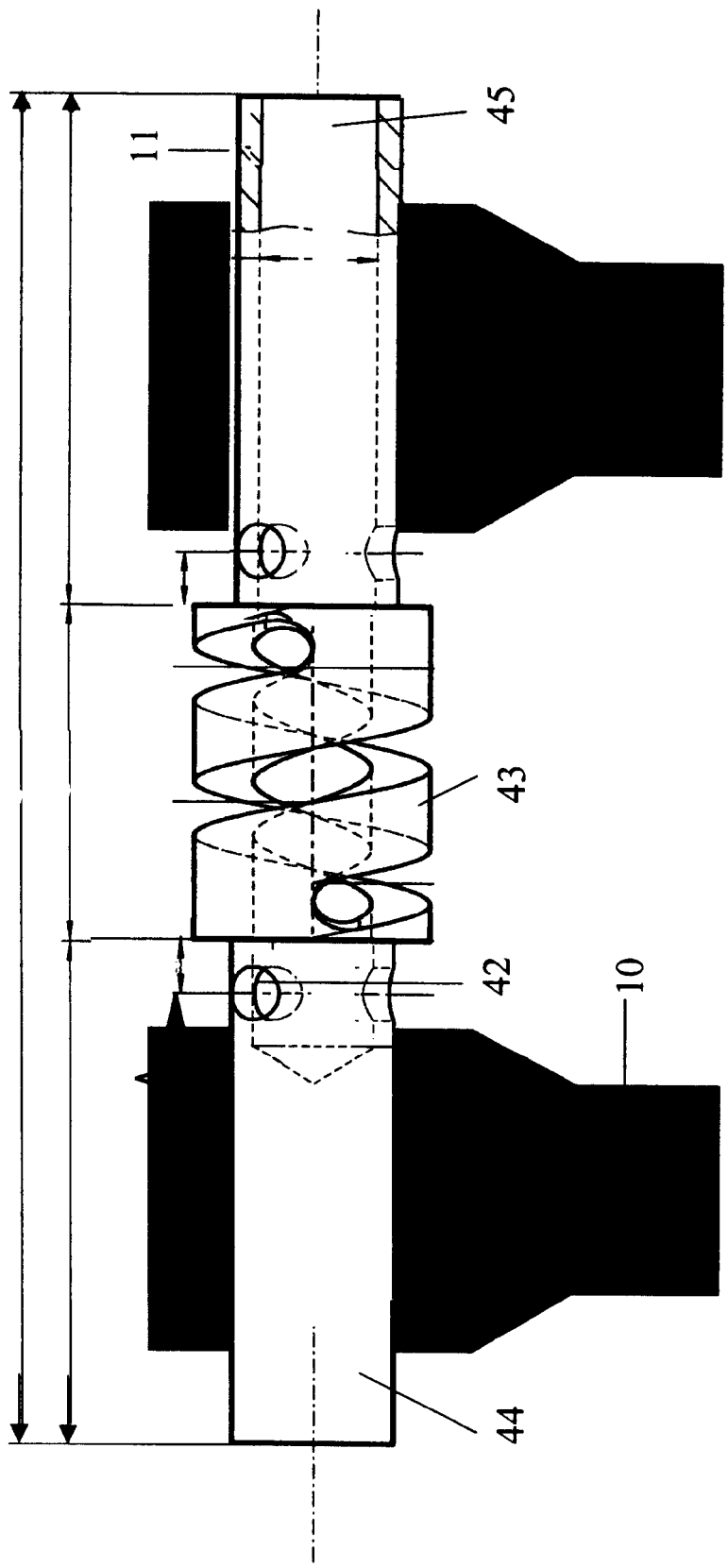
FIG. 15 is a diagrammatic side view of a ninth embodiment of a longitudinal member having an enlarged spiral portion, and contained within a diagrammatic cross-section of two anchoring members.

In the embodiments of FIGS. 11-20, the spiral preferably has a pitch of about 4 mm to about 6 mm, more preferably about 5 mm. The length of the longitudinal member is preferably about 47 mm to about 53 mm, more preferably about 50 mm for single level applications. The length may be changed depending upon many factors, including the size of the patient and the number of discs or vertebrae effected. The width of the spiral wire is preferably about 1 mm to about 3 mm, more preferably about 2 mm. The gaps or spacing 46 between the spiral wire is preferably about 1 mm to about 3 mm, more preferably about 2 mm. Preferably at least two revolutions of the spiral are mechanically active. The diameter of cross holes 42 is preferably about 1 mm to about 3 mm, more preferably about 2 mm. The spiral portion of the embodiment of FIG. 15 is preferably about 10 mm in length to about 14 mm in length, more preferably about 12 mm in length. The dimensions described above are merely exemplary to illustrate the structure of devices and features that may be used singularly or in combination with other features and structures. One of ordinary skill would recognize that the embodiments should not be considered limited to these specific dimensions, but may be changed for different applications and conditions.

The longitudinal member can also consist of cross holes 42 at the end of the spiral portion, which can be used for anchorage of the biocompatible plastics material, as depicted in FIGS. 13 and 14. The cross holes may provide relative movement between the metal spiral and the biocompatible plastics material filling.

The hollow spiral portion of the longitudinal member can be filled with biocompatible plastics material via a hollow end 45 of the non-spiral portion 44. By adding biocompatible plastics material to the hollow end 45 of the non-spiral portion 44, the spiral portion 43 and the hollow end of the longitudinal member preferably are filled with biocompatible plastics material, resulting in a longitudinal member whose hollow cavities preferably are completely filled with biocompatible plastics material. The longitudinal member of the embodiments of FIGS. 13 and 14 is also characterized in that the diameter is identical throughout the structure which promotes percutaneous application of the longitudinal member.

As depicted in FIG. 14, the embodiment described above can be constructed to have one or more spiral portions 43 along the length of the longitudinal member 11. One or more spiral portions 43 may be provided along the length of the longitudinal member configured so that they are located between adjacent vertebrae, when implanted, and in addition to or alternatively one or more spiral portions may be provided along the length so that multiple level stabilizations can be performed, for example a two level stabilization as illustrated in FIG. 14.

Figure 16:
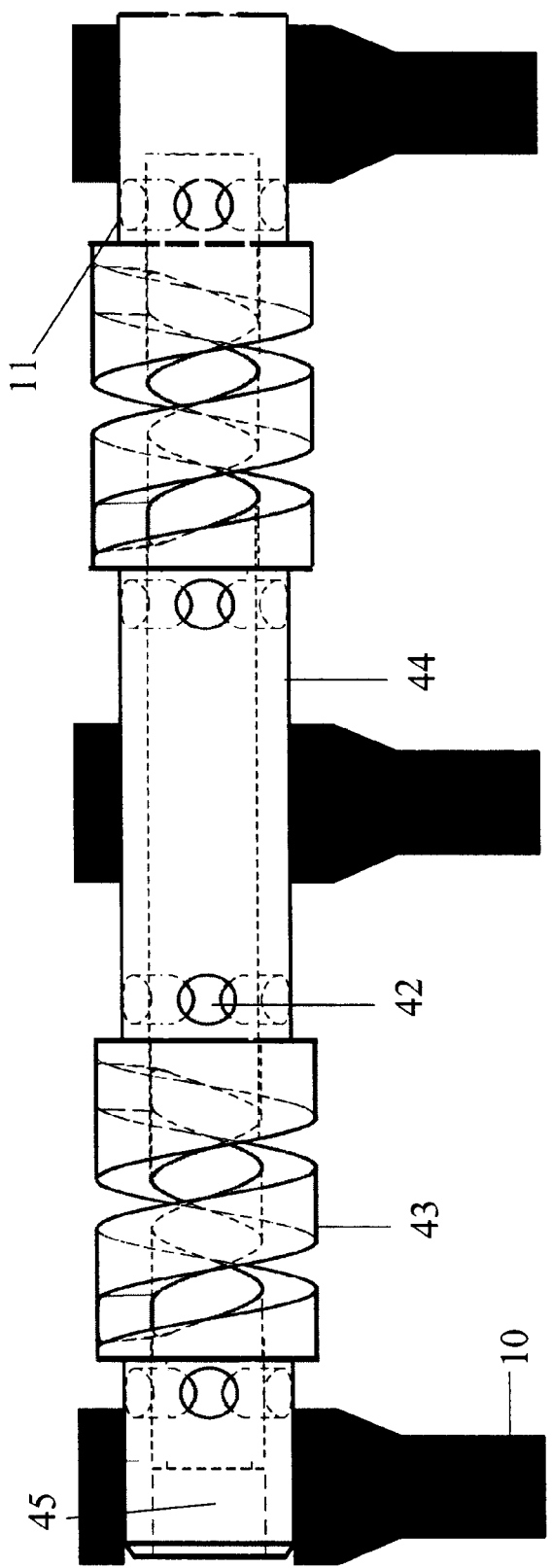
FIG. 16 is a diagrammatic side view of a tenth embodiment of a longitudinal member having an enlarged spiral portion, similar to the longitudinal member of FIG. 14 but configured for a two level stabilization, the longitudinal member contained within a diagrammatic cross-section of three anchor members.

As described above for the embodiments depicted in FIGS. 13 and 14, in the embodiment according to FIGS. 15 and 16, the longitudinal member 11 consists of alternating non-spiral portion 44 and spiral portion 43. In this embodiment the spiral portion 43 is larger in diameter than the non-spiral portion 44. This construction provides for greater flexibility and dynamic movement of the device. Since the longitudinal member consists of two diameters, percutaneous application of the longitudinal member may be difficult, and transitions (not shown) such as tapered regions may be provided. Preferably the spiral portion is sealed against body fluids and the like.

As depicted in FIG. 16, the embodiment described above can be constructed to have one or more spiral portions 43 along the length of the longitudinal member 11. One or more spiral portions 43 may be provided along the length of the longitudinal member configured so that they are located between adjacent vertebrae, when implanted, and in addition to or alternatively one or more spiral portions may be provided along the length so that multiple level stabilizations can be performed, for example a two level stabilization as illustrated in FIG. 16.

Figure 17:
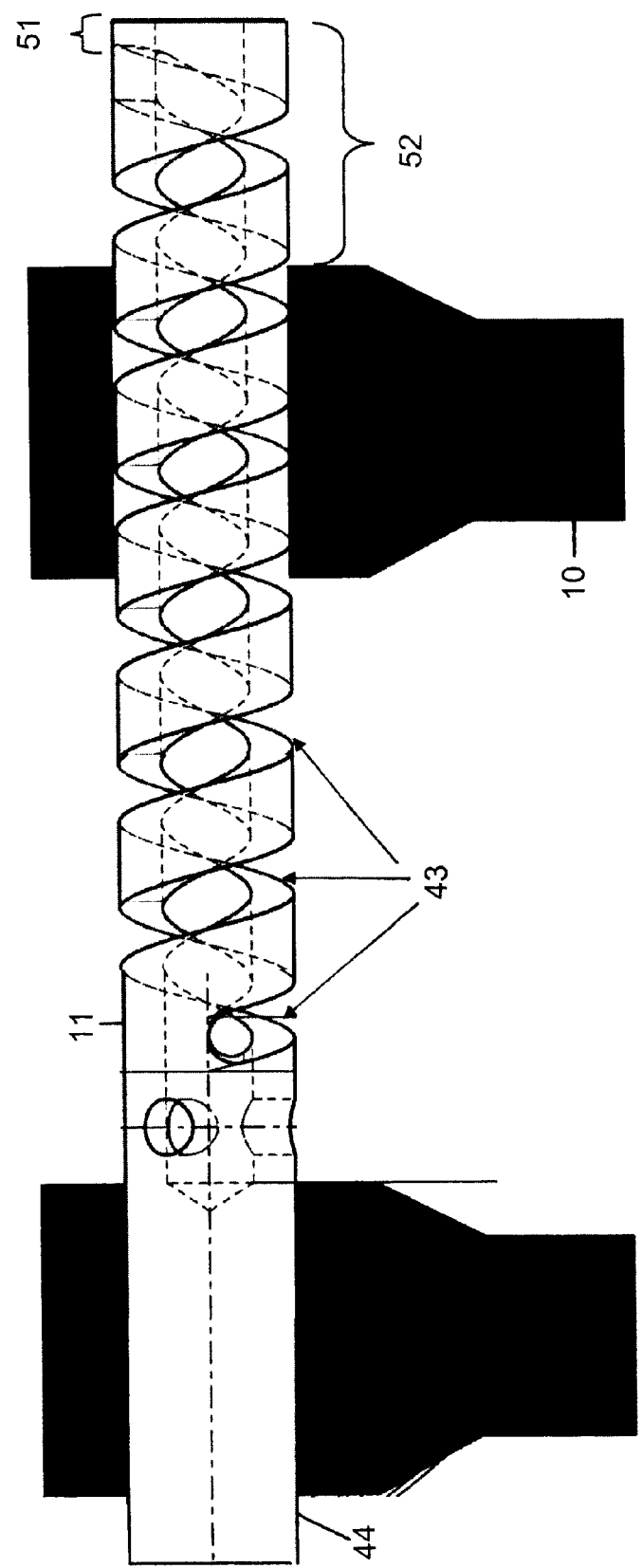
FIG. 17 is a diagrammatic side view of an eleventh embodiment of a longitudinal member contained within diagrammatic cross section of anchoring members.

In the embodiment according to FIG. 17, the longitudinal member 11 consists of non-spiral portion 44 and spiral portion 43, wherein the non-spiral portion 44 is located at one end of the spiral portion 43. The spiral portion 43 is structured as described above for the embodiments of FIGS. 11 and 12. The non-spiral portion 44 of the longitudinal member can be structured as described for prior embodiments above. The end 51 of the spiral portion 43 which is most distal to the non-spiral portion 44 can be inflexible and may consist of an overhang 52 from the pedicle screw 10 that may be at least 5 mm in length.

At least one pedicle screw can be located anywhere along the non-spiral portion 44. The remaining pedicle screws 10 can be positioned anywhere along the length of the spiral portion 43. The longitudinal member 11 preferably has the same diameter throughout the structure which promotes percutaneous application of the longitudinal member. The longitudinal member 11 can be locked in the pedicle screws 10 using a clamping mechanism as described above.

Figure 18:
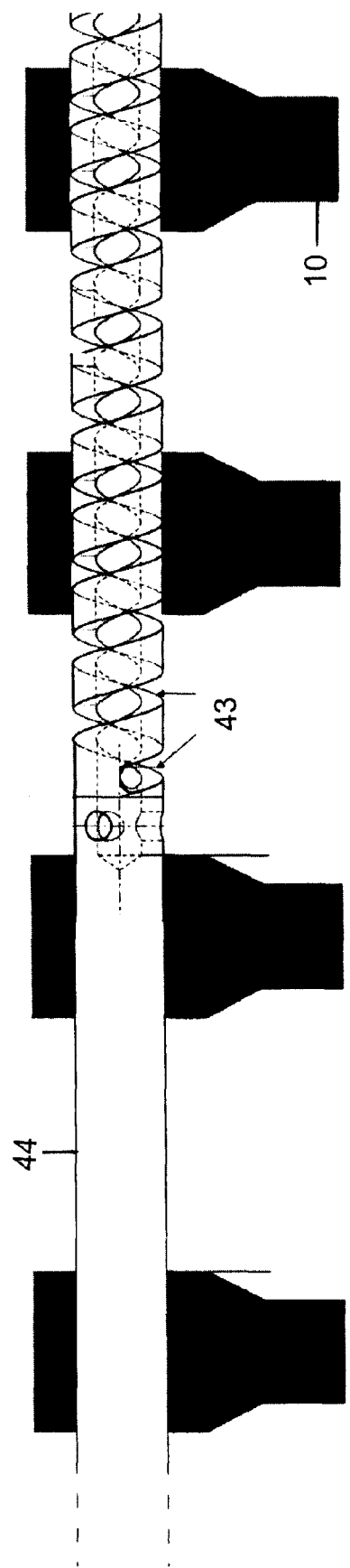
FIG. 18 is a diagrammatic side view of a twelfth embodiment of a longitudinal member contained within diagrammatic cross section of anchoring members.

As depicted in FIG. 18, the embodiment described above can be constructed to have one or more non-spiral portions 44 and one or more spiral portions 43 along the length of longitudinal member 11 such that multiple level stabilizations can be performed, for example a three level stabilization as illustrated in FIG. 18. This structure can provide both inflexible or fusion stabilization through the use of the non-spiral portions, as well as more flexible or dynamic stabilization through the use of the spiral portions. The spiral portion 43 is structured as described above for the embodiments of FIGS. 11 and 12. The spiral portion 43 can be constructed as in FIGS. 15 and 16. The non-spiral portion 44 of the longitudinal member can be structured as described for prior embodiments above.

In the embodiment according to FIGS. 19A, 19B and 19C, the longitudinal member can be structured as described above for the embodiment of FIG. 13 wherein the longitudinal member 11 consists of alternating non-spiral portion 44 and spiral portion 43. A locking cap 55 or a solid rod extension 56 may be inserted into one end of the non-spiral portion 44, as depicted in FIGS. 19A and 19B or into both ends as depicted in FIG. 19C.

As depicted in FIG. 20A, the embodiment described above can be constructed to have one or more spiral portions 43 along the length of the longitudinal member 11. One or more spiral portions 43 may be provided along the length of the longitudinal member configured so that, when implanted, they are located between adjacent vertebrae and in addition to or alternatively one or more spiral portions may be provided along the length so that multiple level stabilizations can be performed, for example a two level stabilization as illustrated in FIG. 20A. A locking cap 55 or a solid rod extension (not shown) may be inserted into one end of the non-spiral portion 44 (not shown), or into both ends as depicted in FIG. 20A.

In the embodiment according to FIGS. 20B and 20C, the longitudinal member is structured similar to the longitudinal member as described above for the embodiment of FIG. 20A. The longitudinal member 11 may consist of two or more units consisting of alternating spiral portions 43 and non-spiral portions 44. The longitudinal member units may be connected to each other via a connecting plug 58. The connecting plug 58 when the longitudinal member is implanted may be located at the pedicle screw 10. A locking cap 55 or a solid rod extension (not depicted) may be inserted into one end of the non-spiral portion 44, as depicted in FIG. 20C or into both ends as depicted in FIG. 20B.

The present invention has been described in connection with the preferred embodiments. These embodiments, however, are merely for example and the invention is not restricted thereto. It will be understood by those skilled in the art that other variations and modifications can easily be made within the scope of the invention as defined by the appended claims, thus it is only intended that the present invention be limited by the following claims.

LIST OF REFERENCE SYMBOLS

V Vertebra
S Spine
10 pedicle screw
11 longitudinal member
12 plastics rod
13 metal collar
14 double-headed arrow
15 stabilization system
16 Interruption
17 metal cap
18 circular surface
19 Flat profile
20 w-shaped elements
21 central member
22 support surface
23 outer surface
24 connecting member
25 clamp
25' clamp
26 metal rod
27 metal disc
28 through-hole
29 supporting or spacer element
30 recess
31 metal rod
32 metal sleeve
33 longitudinal recess
34 longitudinal element
35 connecting element
36 longitudinal hole
37 articulated connection
38 End cap
39 plastics material
40 thickened portion
41 sleeve-like portion
42 cross holes
43 spiral portion
44 non-spiral portion
45 hollow end
46 gap or spacing
50 hollow cavity
51 end of spiral portion
52 overhang
55 locking cap
56 solid rod extension
58 connecting plug

I claim:

1. A device for dynamic stabilization of bones or bone fragments comprising:
   first and second anchor members for attachment to first and second vertebrae, respectively, each anchor member having an opening configured to receive a portion of a longitudinal member; the longitudinal member being viscoelastically deformable and having a predetermined bending resilience, the longitudinal member comprising:
   a plastic rod and a metal band helically wound around the plastic rod, the metal band being embedded in the plastic rod such that the metal band forms with the plastic rod a continuously smooth surface, the metal band including a plurality of interruptions which are filled with a biocompatible plastics material; wherein the biocompatible plastics material has a tensile strength at 50% elongation of about 650 psi to 5500 psi.

2. The device of claim 1, wherein the metal band is manufactured from titanium or titanium alloy.

3. The device of claim 1, wherein the longitudinal member further comprises first and second clamping portions which are is supported directly by the metal band of the longitudinal member.

4. The device of claim 1, wherein the biocompatible plastics material comprises polycarbonate-urethane, polyether-urethane, silicone-urethane copolymer, or a mixture thereof.

5. The device of claim 1, wherein the longitudinal member has first and second ends comprising metal caps or metal discs.

6. A device for dynamic stabilization of bones or bone fragments comprising:
   first and second anchor members for attachment to first and second vertebrae, respectively, each anchor member having an opening configured to receive a portion of a longitudinal member; the longitudinal member being viscoelastically deformable and having a predetermined bending resilience, the longitudinal member comprising:
   a plastic rod and a metal band helically wound around the plastic rod, the metal band being embedded in the plastic rod such that the metal band forms with the plastic rod a continuously smooth surface, the metal band including a plurality of interruptions which are filled with a biocompatible plastics material, wherein the biocompatible plastics material has a tensile strength at 100% elongation of about 9000 psi to 6000 psi.

7. A device for dynamic stabilization of bones or bone fragments comprising:
first and second anchor members for attachment to first and second vertebrae, respectively, each anchor member having an opening configured to receive a portion of a longitudinal member; the longitudinal member being viscoelastically deformable and having a predetermined bending resilience, the longitudinal member comprising:
a plastic rod and a metal band helically wound around the plastic rod, the metal band being embedded in the plastic rod such that the metal band forms with the plastic rod a continuously smooth surface, the metal band including a plurality of interruptions which are filled with a biocompatible plastics material, wherein the biocompatible plastics material has an ultimate tensile strength of about 6500 psi to 11000 psi.

8. A device for dynamic stabilization of bones or bone fragments comprising:
first and second anchor members for attachment to first and second vertebrae, respectively, each anchor member having an opening configured to receive a portion of a longitudinal member; the longitudinal member being viscoelastically deformable and having a predetermined bending resilience, the longitudinal member comprising:
a plastic rod and a metal band helically wound around the plastic rod, the metal band being embedded in the plastic rod such that the metal band forms with the plastic rod a continuously smooth surface, the metal band including a plurality of interruptions which are filled with a biocompatible plastics material, wherein the biocompatible plastics material has an ultimate limit of elongation of about 250% to 600%.

9. A device for dynamic stabilization of bones or bone fragments comprising:
first and second anchor members for attachment to first and second vertebrae, respectively, each anchor member having an opening configured to receive a portion of a longitudinal member; the longitudinal member being viscoelastically deformable and having a predetermined bending resilience, the longitudinal member comprising:
a plastic rod and a metal band helically wound around the plastic rod, the metal band being embedded in the plastic rod such that the metal band forms with the plastic rod a continuously smooth surface, the metal band including a plurality of interruptions which are filled with a biocompatible plastics material, wherein the biocompatible plastics material has a modulus of elasticity of about 4000 psi to 270000 psi.

10. A device for dynamic stabilization of bones or bone fragments comprising:
first and second anchor members for attachment to first and second vertebrae, respectively, each anchor member having an opening configured to receive a portion of a longitudinal member; the longitudinal member being viscoelastically deformable and having a predetermined bending resilience, the longitudinal member comprising:
a plastic rod and a metal band helically wound around the plastic rod, the metal band being embedded in the plastic rod such that the metal band forms with the plastic rod a continuously smooth surface, the metal band including a plurality of interruptions which are filled with a biocompatible plastics material, wherein the biocompatible plastics material has a bending stress on 5% deflection of about 150 psi to 11000 psi.

11. A device for dynamic stabilization of bones or bone fragments comprising:
first and second anchor members for attachment to first and second vertebrae, respectively, each anchor member having an opening configured to receive a portion of a longitudinal member; the longitudinal member being viscoelastically deformable and having a predetermined bending resilience, the longitudinal member comprising:
a plastic rod and a metal band helically wound around the plastic rod, the metal band being embedded in the plastic rod such that the metal band forms with the plastic rod a continuously smooth surface, the metal band including a plurality of interruptions which are filled with a biocompatible plastics material, wherein the longitudinal member can be resiliently deflected while held at one end at about an angle of 5 degrees to 12 degrees over a length of about 2 cm to 5 cm.

* * * * *